United States Patent
Leweke

(10) Patent No.: US 12,377,108 B2
(45) Date of Patent: Aug. 5, 2025

(54) NASAL CANNABIDIOL COMPOSITIONS

(71) Applicant: Franz-Markus Leweke, Bruehl (DE)

(72) Inventor: Franz-Markus Leweke, Bruehl (DE)

(73) Assignee: Curantis UG, Burscheid (DE)

( * ) Notice: Subject to any disclaimer, the term of this patent is extended or adjusted under 35 U.S.C. 154(b) by 0 days.

(21) Appl. No.: 17/649,780

(22) Filed: Feb. 2, 2022

(65) Prior Publication Data

US 2022/0323373 A1    Oct. 13, 2022

Related U.S. Application Data

(63) Continuation of application No. 16/206,948, filed on Nov. 30, 2018, now abandoned.

(51) Int. Cl.
| | |
|---|---|
| *A61K 31/05* | (2006.01) |
| *A61K 9/00* | (2006.01) |
| *A61K 9/06* | (2006.01) |
| *A61K 31/352* | (2006.01) |

(52) U.S. Cl.
CPC ............ *A61K 31/05* (2013.01); *A61K 9/0043* (2013.01); *A61K 9/06* (2013.01); *A61K 31/352* (2013.01)

(58) Field of Classification Search
CPC ...... A61K 31/05; A61K 31/352; A61K 47/14; A61K 47/26; A61K 47/38; A61K 47/44; A61K 9/0043; A61K 9/06; A61K 9/08; A61P 25/18
See application file for complete search history.

(56) References Cited

U.S. PATENT DOCUMENTS

| | | |
|---|---|---|
| 6,383,513 B1 | 5/2002 | Watts et al. |
| 2004/0192760 A1 | 9/2004 | Whittle et al. |
| 2017/0348276 A1* | 12/2017 | Bryson ............... A61K 36/185 |

FOREIGN PATENT DOCUMENTS

| | | | |
|---|---|---|---|
| WO | 1999032107 A1 | 7/1999 | |
| WO | 2002064109 A2 | 8/2002 | |
| WO | 2012156820 A1 | 11/2012 | |
| WO | WO-2017042567 A1 * | 3/2017 | ............ A61K 31/05 |
| WO | 2017208072 A2 | 12/2017 | |

OTHER PUBLICATIONS

Stinchcomb, 2004, XIV Symposium International Cannabinoid Research Society (Year: 2004).*
Bojork-Erisson, Rhinology Dec. 2000;38(4):200-3 (Year: 2000).*
Pires et al (J Pharm Pharmaceut Sci (www.cspsCanada.org) 12(3) 288-311, 2009) (Year: 2009).*
Schönfeld et al (J. Lipid Res. 2016. 57: 943-954) (Year: 2016).*
Leweke et al (Clinical Trial, Tansl Psychiatry, Mar. 20, 2012;2(3): e94). (Year: 2012).*
Bryson et al., U.S. Appl. No. 15/613,116, filed Jun. 2, 2017 (647 pages).
Bjork-Eriksson et al., "Fewer problems with dry nasal mucous membranes following local use of sesame oil", Rhinology; Feb. 25, 2000, pp. 200-203.
Stinchcomb et al., "Evaluation of the Intranasal Delivery of Cannabidiol in Rats", International Cannabinoid Research Society, 14th Annual Symposium on the Cannabinoids, Jun. 22-27, 2004.

* cited by examiner

*Primary Examiner* — Jean P Cornet
(74) *Attorney, Agent, or Firm* — Perkins Coie LLP

(57) ABSTRACT

A nasally administered cannabinoid semi-solid or viscous liquid composition; nasal methods for administering the nasal pharmaceutical compositions; methods for manufacturing the nasal pharmaceutical compositions; and nasal methods of treating diseases treatable by the nasal pharmaceutical compositions formulated with a cannabinoid or mixtures thereof.

6 Claims, 9 Drawing Sheets

STEP 1
BLOW YOUR NOSE TO CLEAR YOUR NOSTRILS

STEP 2
REMOVE THE CAP

STEP 3
PLACE YOUR FINGER ON THE PUMP OF THE ACTUATOR AND, IN FRONT OF A MIRROR, ADVANCE THE TIP OF THE ACTUATOR INTO YOUR LEFT NOSTRIL UNTIL THE FINGER ON THE PUMP REACHES THE BASE OF THE NOSE

STEP 4
AIM THE TIP OF THE ACTUATOR TO THE INNER CORNER OF YOUR LEFT EYE. THE OPENING ON THE TIP OF THE ACTUATOR MUST FACE THE NASAL MUCOSA

STEP 5
DEPRESS THE PUMP UNTIL IT STOPS

STEP 6
SLOWLY REMOVE THE ACTUATOR FROM YOUR NOSE CONTINUE ON REVERSE SIDE

STEP 7
REPEAT THE PROCESS FOR THE RIGHT NOSTRIL

STEP 8
PLACE YOUR FINGER ON THE PUMP OF THE ACTUATOR AND, IN FRONT OF A MIRROR, ADVANCE THE TIP OF THE ACTUATOR INTO YOUR RIGHT NOSTRIL UNTIL THE FINGER ON THE PUMP REACHES THE BASE OF THE NOSE

STEP 9
AIM THE TIP OF THE ACTUATOR TO THE INNER CORNER OF YOUR RIGHT EYE. THE OPENING ON THE TIP OF THE ACTUATOR MUST FACE THE NASAL MUCOSA

FIGURE 7A

STEP 10

DEPRESS THE PUMP UNTIL IT STOPS. SLOWLY REMOVE THE ACTUATOR FROM YOUR NOSE

STEP 11

WIPE AWAY ANY GEL THAT REMAINS ON THE TIP OF THE ACTUATOR USING A CLEAN, DRY SWAB

STEP 12

PRESS THE NOSTRILS NEAR THE BRIDGE OF THE NOSE LIGHTLY TOGETHER AND MASSAGE FOR ONE SECOND DO NOT BLOW YOUR NOSE OR SNIFF FOR ONE HOUR AFTER ADMINISTRATION OF THE MEDICATION

Pharmacokinetic analysis of 10% and 20% CBD in Castor Oil after administration to 4 subjects.

NASAL CANNABIDIOL COMPOSITIONS

CROSS-REFERENCE TO RELATED APPLICATIONS

This application is a continuation of U.S. patent application Ser. No. 16/206,948, entitled "Nasal Cannabidiol Composition," filed on Nov. 30, 2018, the content of which is incorporated by reference in its entirety.

INCORPORATION BY REFERENCE

The following U.S. patent applications and U.S. patents are incorporated herein by reference in their entireties:
U.S. Provisional Application Ser. No. 62/426,403 entitled "CANNABIDIOL NASAL FORMULATIONS";
U.S. Provisional Application Ser. No. 62/344,486 entitled "CANNABIDIOL NASAL FORMULATIONS"; and
U.S. Patent Application Publication No. U.S. 2017/0348276 (U.S. patent application Ser. No. 15/613,116) entitled "CANNABIDIOL NASAL FORMULATIONS".

FIELD OF THE INVENTION

The present invention is directed to cannabinoid pharmaceutical compositions for topical application into the nasal cavity of a subject, nasal methods of use thereof and methods of manufacture. In accordance with the present invention, the nasal cannabinoid compositions of the present invention can be used as medical *cannabis* to treat disorders or disease states or alleviate or mitigate symptoms thereof where it is useful to administer cannabinoid, such as schizophrenia, epilepsy, pain, anxiety, spasticity and migraine. The nasal cannabinoid compositions of the present invention are semi-solid or viscous liquid pharmaceutical compositions, namely, creams, gels and emulsions, preferably thixotropic creams, gels and emulsions, that are formulated with therapeutically effective amounts of cannabinoid and are nasally administered to treat disorders or disease states or alleviate or mitigate symptoms thereof that are treatable with cannabinoid.

BACKGROUND

Endocannabinoid System

The endocannabinoid system is an ancient, evolutionarily conserved, and ubiquitous lipid signaling system found in all vertebrates, and which appears to have important regulatory functions throughout the human body. The endocannabinoid system has been implicated in a very broad number of physiological as well as pathophysiological processes including neural development, immune function, inflammation, appetite, metabolism and energy homeostasis, cardiovascular function, digestion, bone development and bone density, synaptic plasticity and learning, pain, reproduction, psychiatric disease, psychomotor behaviour, memory, wake/sleep cycles, and the regulation of stress and emotional state. The system consists of the cannabinoid 1 and 2 ($CB_1$ and $CB_2$) receptors, the CB receptor ligands N-arachidonoylethanolamine (i.e. anandamide or AEA) and 2-arachidonoylglycerol (2-AG) as well as the endocannabinoid-synthesizing and degrading enzymes fatty acid amide hydrolase (FAAH) and monoacylglycerol lipase (MAGL).

Most tissues contain a functional endocannabinoid system with the $CB_1$ and $CB_2$ receptors having distinct patterns of tissue expression. The $CB_1$ receptor is one of the most abundant G-protein coupled receptors in the central and peripheral nervous systems. It has been detected in the cerebral cortex, hippocampus, amygdala, basal ganglia, substantia nigra pars reticulata, internal and external segments of the globus pallidus and cerebellum (molecular layer), and at central and peripheral levels of the pain pathways including the periaqueductal gray matter, rostral ventrolateral medulla, the dorsal primary afferent spinal cord regions including the peripheral nociceptors, and the spinal interneurons. The $CB_1$ receptor is also expressed in many other organs and tissues including adipocytes, leukocytes, spleen, heart, lung, the gastrointestinal tract (liver, pancreas, stomach, and the small and large intestine), kidney, bladder, reproductive organs, skeletal muscle, bone, joints, and skin. $CB_1$ receptor expression appears to be relatively sparse in the brainstem region. $CB_2$ receptors are most highly concentrated in the tissues and cells of the immune system such as the leukocytes and the spleen, but can also be found in bone and to a lesser degree in liver and in nerve cells including astrocytes, oligodendrocytes and microglia, and even some neuronal sub-populations.

Dysregulation of the endocannabinoid system appears to be connected to a number of pathological conditions, with the changes in the functioning of the system being either protective or maladaptive. Modulation of the endocannabinoid system either through the targeted inhibition of specific metabolic pathways, and/or directed agonism or antagonism of its receptors may hold therapeutic promise. However, a major and consistent therapeutic challenge confronting the routine use of psychoactive cannabinoids (e.g. THC) in the clinic has remained that of achieving selective targeting of the site of disease and the sparing of other bodily regions such as the mood and cognitive centers of the brain.

*Cannabis*

Marihuana (Marijuana) is the common name for *Cannabis sativa* (i.e. *cannabis*), a hemp plant that grows throughout temperate and tropical climates. The leaves and flowering tops of *Cannabis* plants contain at least 489 distinct compounds distributed among 18 different chemical classes, and harbor more than 70 different phytocannabinoids. The principal cannabinoids appear to be delta-9-tetrahydrocannabinol (i.e. $\Delta^9$-THC, THC), cannabinol (CBN), and cannabidiol (CBD), although the relative abundance of these and other cannabinoids can vary depending on a number of factors such as the *Cannabis* strain, the soil and climate conditions, and the cultivation techniques. Other cannabinoids found in *cannabis* include cannabigerol (CBG), cannabichromene (CBC), tetrahydrocannabivarin (THCV) and many others. In the living plant, these phytocannabinoids exist as both inactive monocarboxylic acids (e.g. THCA) and as active decarboxylated forms (e.g. THC); however, heating (at temperatures above 120° C.) promotes decarboxylation (e.g. THCA to THC) and results in biological activation. Furthermore, pyrolysis transforms each of the hundreds of compounds in *cannabis* into a number of other compounds, many of which remain to be characterized both chemically and pharmacologically. Therefore, marihuana (*cannabis*) can be considered a very crude drug containing a very large number of chemical and pharmacological constituents, the properties of which are only slowly being understood.

Among all the chemical constituents of *cannabis*, and particularly among the cannabinoids, $\Delta^9$-THC is by far the best studied and is responsible for many, if not most, of the physical and psychotropic effects of *cannabis*. Other cannabinoids (such as CBD, CBC, CBG) are present in lesser amounts in the plant and have little, if any, psychotropic properties. It is reasonable to consider about 10% (range 1-30%) as an average for $\Delta^9$-THC content in *cannabis* found on the illicit market. The dried marihuana currently provided by Health Canada is composed of the mature flowering heads of female plants and contains 12.5±2% total THC ($\Delta^9$-THC and $\Delta^9$-THCA), and less than 0.5% CBD, CBG, CBN, and CBC.

Much of the pharmacodynamic information on *cannabis* refers to the effects of the major constituent $\Delta^9$-THC which acts as a partial agonist at both CB receptors, has activity at non-CB receptors and other targets, and is responsible for the psychoactive effects of *cannabis* through its actions at the $CB_1$ receptor. $\Delta^8$-THC (an isomer of $\Delta^9$-THC) is found in smaller amounts in the plant, but like $\Delta^9$-THC, it is a partial agonist at both CB receptors and shares relatively similar efficacy and potency with $\Delta^9$-THC in in vitro assays. An in vivo animal study and one clinical study suggest $\Delta^8$-THC to be a more potent anti-emetic than $\Delta^9$-THC.

Cannabinol (CBN) is a product of $\Delta^9$-THC oxidation and has 10% of the activity of $\Delta^9$-THC. Its effects are not well studied but it appeared to have some possible immunosuppressive properties in a small number of in vitro studies. Cannabigerol (CBG) is a partial $CB_{1/2}$ receptor agonist and a small number of in vitro studies suggest it may have some anti-inflammatory and analgesic properties. It may also block $5\text{-}HT_{1A}$ receptors and act as an $\alpha_2$-adrenoceptor agonist.

Cannabidiol (CBD) lacks detectable psychoactivity and does not appear to bind to either $CB_1$ or $CB_2$ receptors at physiologically meaningful concentrations, but it affects the activity of a significant number of other targets including ion channels, receptors, and enzymes. Results from pre-clinical studies suggest CBD has anti-inflammatory, analgesic, anti-nausea, anti-emetic, anti-psychotic, anti-ischemic, anxiolytic, and anti-epileptiform effects.

Tetrahydrocannabivarin (THCV) acts as a $CB_1$ receptor antagonist and $CB_2$ receptor partial agonist in vitro and in vivo, and pre-clinical studies suggest it may have anti-epileptiform/anti-convulsant properties.

Much of what is known about the beneficial properties of cannabinoids (e.g. CBD, THCV) is derived from in vitro and animal studies and few, if any, clinical studies of these substances exist. However, the results from these in vitro and animal studies point to potential therapeutic indications such as psychosis, epilepsy, anxiety, sleep disturbances, neurodegeneration, cerebral and myocardial ischemia, inflammation, pain and immune responses, emesis, food intake, type-1 diabetes, liver disease, osteogenesis, and cancer.

In general, there appear to be two types of mechanisms which could govern possible interactions between CBD and $\Delta^9$-THC: those of a pharmacokinetic origin, and those of a pharmacodynamic origin. Despite the limited and complex nature of the available information, it generally appears that pre-administration of CBD may potentiate some of the effects of THC (through a pharmacokinetic mechanism), whereas simultaneous co-administration of CBD and THC may result in the attenuation of some of the effects of THC (through a pharmacodynamic mechanism). Furthermore, the ratio between the two phytocannabinoids also appears to play a role in determining whether the overall effect will be of a potentiating or antagonistic nature. CBD-mediated attenuation of THC-induced effects may be observed when the ratio of CBD to THC is at least 8:1 (±11.1), whereas CBD appears to potentiate some of the effects associated with THC when the CBD to THC ratio is around 2:1 (±1.4). Potentiation of THC effects by CBD may be caused by inhibition of THC metabolism in the liver, resulting in higher plasma levels of THC.

Cannabidiol

Cannabidiol (CBD) is one of 85 phytocannabinoids found in the *cannabis* plant (Iseger 2015). While there is a rich history of *cannabis* use for medicinal purposes, a focus on CBD has not arisen until recently, as it became known as the main non-psychoactive cannabinoids found within *Cannabis sativa* (Iseger 2015). CBD also has a close relation to the other major component of such *cannabis* plants, $\Delta^9$-tetrahydrocannabinol (THC). While CBD is typically administered orally, the oral bioavailability is believed to be <5% due to extensive first pass hepatic metabolism. Cannabidiol has the following formula:

FORMULA 1

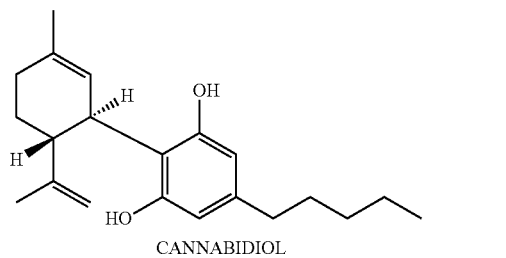

CANNABIDIOL

Medicinal preparations from the flowers and resin of *C. sativa* have been used in China since ~2700 BCE to treat menstrual disorders, gout, rheumatism, malaria, constipation, and absent-mindedness. In medieval times, Islamic physicians used *cannabis* to treat nausea and vomiting, epilepsy, inflammation, pain, and fever. Western medicine used *cannabis* widely in the 1800s; before aspirin, it was a common analgesic drug. More recently, *cannabis* has been used to treat glaucoma, pain, nausea and vomiting, muscle spasms, insomnia, anxiety, and epilepsy. Evidence for efficacy varies substantially for different indications, with the best data in painful HIV-associated sensory neuropathy, chronic pain, chemotherapy-induced nausea and vomiting, and spasms in patients with multiple sclerosis. Other medicinal uses for *cannabis* have been proposed, but none has been examined in well-controlled clinical trials.

CBD and Schizophrenia

Schizophrenia is a chronic mental disorder that typically presents in early adulthood or late adolescence. Although the incidence of schizophrenia is relatively low (10-22 per 100,000), its prevalence is relatively high (0.3-0.7 per 100) due to the chronic nature of the illness (McGrath et al., 2008). Schizophrenia is characterized by a wide range of symptoms, including disturbances of thought, perception, volition, and cognition (see for reviews Tandon et al., 2009; van Os and Kapur, 2009). Because of the pervasiveness of associated impairments and frequently life-long course, it is among the top ten leading causes of disease-related disability in the world. Although extensive research has been performed, its etiology and pathophysiology remain relatively unclear, and available treatments are only modestly effective and cause serious metabolic and neurological adverse effects (Tandon et al., 2008).

There is current belief that the endocannabinoid system may have a role in the pathophysiology of schizophrenia (Leweke and Koethe, 2008; Bossong and Niesink, 2010). For example, epidemiological studies indicate that the use of *cannabis* increases the risk for developing schizophrenia (Arseneault et al., 2004; Moore et al., 2007) and lowers the age of onset of the illness (Veen et al., 2004). In patients, *cannabis* use has been related to higher relapse rates, poor treatment outcome, and increased severity of symptoms (Linszen et al., 1994; D'Souza et al., 2005; Foti et al., 2010), as well as accelerated loss of grey matter volume (Rais et al., 2008). In addition, schizophrenia patients show increased levels of endogenous cannabinoids in cerebrospinal fluid (Leweke et al., 1999; Giuffrida et al., 2004). Autoradiography studies with post-mortem brain tissue show enhanced $CB_1$ receptor densities in schizophrenia patients, with significant increases demonstrated in the dorsolateral prefrontal cortex (Dean et al., 2001; Dalton et al., 2011; Jenko et al., 2012), anterior cingulate cortex (Zavitsanou et al., 2004) and posterior cingulate cortex (Newell et al., 2006). Neuroimaging studies measuring in vivo $CB_1$ receptor availability in schizophrenia patients report a widespread increase in levels of $CB_1$ receptors, including the nucleus accumbens, insula, cingulate cortex, inferior frontal cortex, parietal cortex, mediotemporal lobe and pons (Wong et al., 2010; Ceccarini et al., 2013).

Cannabidiol (CBD), a major non-psychotomimetic cannabinoid compound extracted from *Cannabis sativa*, may present potential therapeutic effects in the treatment of schizophrenia. CBD is a phytocannabinoid, accounting for up to 40% of the plant's extract. Several pre-clinical studies have suggested that this drug induces antipsychotic-like effects (for review see Campos et al., 2012). These CBD effects have also been described in open-label clinical studies (Zuardi et al., 1995, 2006) and in a recent controlled, randomized, double-blind clinical trial (Leweke et al., 2012). The mechanism of these effects is still unknown (Campos et al., 2012). CBD is believed to have anxiolytic and antipsychotic properties while being devoid of any psychotropic effects (Zuardi et al., 2012; Schubart et al., 2014). Although the mode of action of CBD is not fully understood, there is belief that CBD acts as a cannabinoid $CB_1/CB_2$ receptor inverse agonist (Pertwee, 2008), and that CBD inhibits the uptake and metabolism of anandamide, thereby enhancing levels of endogenous cannabinoids (Bisogno et al., 2001; de Petrocellis et al., 2011; Leweke et al., 2012).

Besides its antipsychotic properties, CBD is also believed to possibly induce anti-inflammatory and neuroprotective effects A considerable number of preclinical studies have suggested that CBD attenuates or increases glial reactivity associated to pathological conditions (Mecha et al., 2013; Perez et al., 2013; Schiavon et al., 2014).

CBD and Epilepsy

Epilepsy is a chronic neurological disorder presenting a wide spectrum of diseases that affects approximately 50 million people worldwide (Sander, 2003). Advances in the understanding of the body's internal 'endocannabinoid' system have led to the suggestion that some *cannabis*-based medicines may have the potential to treat this disorder of hyperexcitability in the central nervous system (Mackie, 2006, Wingerchuk, 2004, Alger, 2006).

It is believed that CBD is the only non-$\Delta^9$-THC phytocannabinoid to have been assessed in preclinical and clinical studies for anticonvulsant effects. It has been reported that oral CBD may be effective against both PTZ- and MES-induced seizures, but one study has showed no effect on PTZ- or MES-induced seizures CBD combined with THCV has been proposed as a means of treating epilepsy. See, e.g., U.S. patent application Ser. No. 13/380,305, entitled "Use of One or a Combination of Phyto-Cannabinoids in the Treatment of Epilepsy", filed on 9 Jun. 2010 and published as U.S. Patent Publication No. 20120165402 on 28 Jun. 2012, which is incorporated herein by reference in its entirety. See, also, U.S. patent application Ser. No. 15/183,947, entitled "Use of Cannabinoids in the Treatment of Epilepsy", filed on 16 Jun. 2016 and published as U.S. Patent Publication No. 2017/0007551 on 12 Jan. 2017; U.S. patent application Ser. No. 14/881,969, entitled "Use of Cannabinoids in the Treatment of Epilepsy", filed on 13 Oct. 2015 and published as U.S. Patent Publication No. 2016/0166515 on 16 Jun. 2016; U.S. patent application Ser. No. 14/881,954, entitled "Use of Cannabinoids in the Treatment of Epilepsy", filed on 13 Oct. 2015 and published as U.S. Patent Publication No. 2016/0166514 on 16 Jun. 2016; U.S. patent application Ser. No. 14/741,829, entitled "Use of Cannabinoids in the Treatment of Epilepsy", filed on 17 Jun. 2015 and published as U.S. Patent Publication No. 2015/0359756 on 17 Dec. 2015; U.S. patent application Ser. No. 14/579,061, entitled "Use of One or a Combination of Phyto-Cannabinoids in the Treatment of Epilepsy", filed on 22 Dec. 2014 and published as U.S. Patent Publication No. 2015/0335590 on 26 Nov. 2015; U.S. patent application Ser. No. 14/741,783, entitled "Use of Cannabinoids in the Treatment of Epilepsy", filed on 17 Jun. 2015 and published as U.S. Patent Publication No. 2015/0359755 on 17 Dec. 2015; U.S. patent application Ser. No. 13/977,766, entitled "Use of the Phytocannabinoid Cannabidiol (Cbd) in Combination with a Standard Anti-Epileptic Drug (Saed) in the Treatment of Epilepsy", filed on 3 Jan. 2012 and published as U.S. Patent Publication No. 2014/0155456 on 5 Jun. 2014; and U.S. patent application Ser. No. 13/977,766, entitled "Use of the Phytocannabinoid Cannabidiol (Cbd) in Combination with a Standard Anti-Epileptic Drug (Saed) in the Treatment of Epilepsy", filed on 3 Jan. 2012 and published as U.S. Patent Publication No. 2013/0296398 on 7 Nov. 2013; each of which is incorporated herein by reference in its entirety.

CBD Compositions

CBD can be administered orally, yet the oral bioavailability is believed to be <5% due to extensive first pass hepatic metabolism (Karschner et al., 2011, Clin. Chem. 57:66-75). CBD has been delivered orally in an oil-based capsule in some human trials, but low water solubility and absorption from the gastrointestinal system lead to erratic and variable pharmacokinetics. Bioavailability from oil-based oral delivery has been estimated at 6% due to significant first-pass metabolism in the liver. Oral-mucosal/sublingual delivery through sprays/lozenges has similar bioavailability to the oral route but is reported as less variability, up to 12% (Mannila et. Al. 2005 Eur. J. Pharm. Sci., 26, 71). Smoking typically delivers cannabinoids at an average bioavailability rate of 30% (Huestis, 2007, Chem. Biodivers. 4:1770-1804; McGilveray 2005, Pain Res. Manag. 10 Suppl. A:15A-22A).

Oral-mucosal delivery comes from studies of Sativex® oral spray, which is a mixture of ~1:1 THC and CBD. Specifically, the studies were of serum CBD levels in healthy volunteers after a single dose of Sativex containing a 1:1 ratio of CBD and THC. 10.8 mg CBD is believed to produce a Cmax of 2.5 to 3.0±3.1 pg/L and Tmax of 2.8±1.3 hrs. See, e.g., E. L. Karschner et al.: Plasma Cannabinoid Pharmacokinetics following Controlled Oral $\Delta^9$-Tetrahydrocannabinol and Oromucosal *Cannabis* Extract Administration. Clin Chem. 2011 January; 57(1): 66-75; see also Public Information Report on Sativex® Oromucosal Spray available at http://www.mhra.gov.uk/home/groups/par/documents/websiteresource/con2033379.pdf; both of which are incorporated herein in their entireties. Oral-mucosal forms are believed to have undesireable side effects including bad taste and dry mouth/sores possibly due to the alcohol content.

Other Cannabinoid Compositions

Cannabinoids, such as THC and CBD are largely consumed by smoking or vaporizing of dried *cannabis* plant material (leafs, stems, flower). The active components of *cannabis* can be extracted with alcohols and applied in the oral cavity. The active components can be extracted into oils for use in oral administration (as an additive to food or baked goods). Pharmaceutical preparations in oils may come in the form of, e.g., gelatin capsules for oral administration (Marinol®).

Smoked or vaporized *cannabis* releases a distinct odor that may be unpleasant and clearly identifies the user. Oral administration has variable absorption due to the highly lipophilic nature of most cannabinoids, THC and CBD in particular. The oral-mucosal spray can cause drying of mucosal tissues and a burning sensation, particularly if there are any open sores or during upon repeat chronic usage.

Transdermal approaches to CBD delivery have also been investigated, but due to CBD's high lipophilicity, special ethosomal delivery systems are needed to prevent drug accumulation in the skin, which are believed to be impractical and costly at this time.

CBD can also be obtained for treatment by smoking CBD-enriched marijuana, however, particularly in the case of treatment of psychotic patients this is a discouraged route of administration as it may lead to further abuse of THC and further relapses in psychosis.

Thus, there is a need for alternative means of administration of the drug that does not require smoking or oral-mucosal administration; preferably, the alternative forms of administration should be convenient to the user, discreet, increase bioavailbility over known forms of administration, and at least as safe as other known methods.

Nasal Administration

Methods of nasal administration of hormone-based drugs are known, for example, an oil-based vehicle for testosterone is described in U.S. patent application Ser. No. 13/194,928 and PCT Application No. PCT/162012/001127, which are incorporated herein by reference in their entireties.

SUMMARY OF THE INVENTION

The present invention overcomes the limitations and disadvantages associated with the treatment of medical *cannabis* therapies available today through the discovery of novel nasal pharmaceutical compositions for topical application into the nasal cavity of a subject, namely humans. Particularly, the present invention overcomes the limitations and disadvantages of currently available options for administration of *cannabis* through the discovery of novel and improved nasal pharmaceutical composition, specifically designed for intranasal administration to deliver therapeutically effective amounts of cannabinoid to treat subjects who suffer from and/or have been diagnosed with anti-psychosis, epilepsy, schizophrenia, anxiety, sleep disturbances, neurodegeneration, cerebral and myocardial ischemia, inflammation, pain including chronic pain, immune responses, emesis, food intake, such as appetite stimulation in HIV/AIDS, type-1 diabetes, liver disease, osteogenesis, glaucoma, cancer, conditions relating to certain types of cancer, including nausea and vomiting, a movement disorder, depression, a mood disorder or a psychological disorder and Tourette syndrome.

The present invention relates to a system for dispensing intranasally a precise dosage amount of such nasal pharmaceutical compositions at an optimal anatomical location within each nostril of the subject, so that an effective amount of the cannabinoid is deposited within each nostril at the optimal anatomical location, i.e., the nasal vestibule, to use the nasal pharmaceutical compositions as medical *cannabis* to effectively treat subjects to treat disease states or alleviate or mitigate symptoms thereof treatable with *cannabis*.

The term "a therapeutically effective amount" means an amount of cannabinoid containing THC and/or CBD sufficient to induce a therapeutic or prophylactic effect in treating or to alleviating or mitigating symptoms associated with anti-psychosis, epilepsy, schizophrenia, arthritis, asthma, antipsychosis, anxiety, sleep disturbances, neurodegeneration, psychosis, depression, glaucoma, neurodegeneration, cerebral and myocardial ischemia, inflammation, immune response, emesis, food intake, such as appetite stimulation in HIV/AIDS, diabetes), liver disease, osteogenesis, cancer conditions relating to certain types of cancer including nausea and vomiting, a movement disorder, a mood disorder), a psychological disorder and Tourette syndrome.

Thus, generally speaking, the present invention provides for new and improved, substantially less-irritating, cannabinoid semi-solid or viscous liquid nasal pharmaceutical compositions formulated with cannabinoid in amounts ranging from between about 0.1% to about 25% or more by weight, for nasal administration to deliver a therapeutically effective amount of cannabinoid to effectively treat disorders or disease states treatable with cannabinoid or to alleviate or mitigate symptoms associated therewith. The present invention is also directed to novel methods for pernasal administration of the nasal cannabinoid pharmaceutical compositions. Generally speaking, the novel methods involve depositing the nasal cannabinoid pharmaceutical compositions topically into the nasal cavity of each nostril to deliver a therapeutically effective amount of cannabinoid, e.g., from about 0.5 mg/nostril to about 37.5 mg/nostril per application delivered in a dose amount ranging from about 50 µl/per nostril to about 150 µl/nostril or from about 0.1%/50 µl per nostril per application to about 25%/150 µl per nostril per application, over dose life for providing constant effective cannabinoid brain and/or blood levels for use in cannabinoid therapy.

In accordance with the novel methods of the present invention, the intranasal cannabinoid nasal pharmaceutical compositions are topically deposited on the outer external walls (opposite the nasal septum) inside the naval cavity of each nostril, preferably at about the middle to about the upper section of the outer external wall (opposite the nasal septum) just under the cartilage section of the outer external wall inside the naval cavity of each nostril. Once nasal pharmaceutical composition deposition is complete within each nostril of the nose, the outer nose is then gently and carefully squeezed and/or rubbed by the subject, so that the deposited nasal pharmaceutical composition remains in contact with the mucosal membranes within the nasal cavity for sustained release of the cannabinoid over dose life. Typical cannabinoid nasal pharmaceutical composition dosage amounts deposited pernasal application is between about 50 to about 150 microliters per nostril, and preferably about 100 microliters per nostril.

In carrying out the methods of the present invention, approximately between 50 microliters and about 150 microliters of a nasal cannabinoid pharmaceutical composition of the present invention is applied to each nostril of a subject once, twice, three times, four times, five times, six times, seven times, eight times of more daily, e.g., for one, two, three, four or more consecutive weeks, or for two, three, four, five or six consecutive months or more, or intermittently such as every other day or once, twice or three times weekly, or on demand, to the cannabinoid treatable disorders.

While the present invention has identified what it believes to be preferred concentrations of intranasal cannabinoid compositions, numbers of applications per day, durations of therapy, pernasal methods and pre-filled, multi-dose applicator systems, it should be understood by those versed in this art that any effective dosage concentration of a cannabinoid or mixtures thereof, e.g., between about 0.1% and about 25% % by weight, in an intranasal composition that delivers an effective amount of cannabinoid or mixtures thereof and any numbers of applications per day, week, month or year, as described herein, that can effectively treat cannabinoid treatable disorders without causing unwanted cannabinoid treatment limiting reactions or related adverse events is contemplated by the present invention.

The present invention therefore provides for a new and improved treatment for cannabinoid treatable disorders, wherein nasal administration of a nasal cannabinoid pharmaceutical composition of the present invention provides for: (1) rapid delivery of cannabinoid due to the highly permeable nasal tissue both systemically and across the blood-brain barrier into the brain; (2) fast onset of action; (3) avoidance of hepatic first-pass metabolism; (4) ease of administration; (5) avoidance of irritation from transdermal administration and no local irritability from topical patch products; and (6) a more pleasant mode of administration, as compared to inhalation, topical skin applications and buccal or sublingual tablets.

In other words, the present invention provides for a new and improved cannabinoid treatment that (a) is easy and convenient to use either according to a prescribed treatment regimen or on-demand, (b) rapidly delivers therapeutically effective amounts of cannabinoid or mixtures thereof, (c) provides for simple use, (d) has reduced side effects associated with prior inhalation and exogenous systemic cannabinoid therapies, (e) avoids local irritability associated with prior topical cannabinoid compositions, and (f) eliminates the need for embarrassing inhalation therapies.

The present invention, in one embodiment, provides numerous surprising advantages over currently available cannabinoid therapies. For example, the present invention provides for (1) a rapid increase in the plasma cannabinoid plasma level (e.g., an increase in the plasma cannabinoid to a level of at least about 0.5 ng/ml within about 15 minutes immediately after nasal administration of the nasal cannabinoid pharmaceutical compositions of the present invention); (2) a sustained increase in the plasma cannabinoid plasma level (e.g., an increase in the plasma cannabinoid level that is maintained in a subject for at least about 8 hours following nasal administration of the nasal cannabinoid pharmaceutical compositions of the present invention); and (3) a higher maximum level of plasma cannabinoid as compared to the maximum level of plasma cannabinoid following topical skin administration.

In accordance with the present invention, the nasal cannabinoid pharmaceutical compositions for nasal administration of the invention may further comprise any pharmaceutically acceptable vehicle, excipient and/or other active ingredient.

In addition, the present invention contemplates cannabinoid compositions for nasal administration that are pharmaceutically equivalent, therapeutically equivalent, bioequivalent and/or interchangeable, regardless of the method selected to demonstrate equivalents or bioequivalence, such as pharmacokinetic methodologies, microdialysis, in vitro and in vivo methods and/or clinical endpoints described herein.

Thus, the present invention contemplates nasal cannabinoid pharmaceutical compositions for topical administration into the nasal cavity of a subject that are bioequivalent, pharmaceutically equivalent and/or therapeutically equivalent. Thus, the present invention contemplates: (a) pharmaceutically equivalent nasal cannabinoid pharmaceutical compositions for nasal administration which contain the same amount of cannabinoid in the same dosage form; (b) bioequivalent nasal cannabinoid pharmaceutical compositions for nasal administration which are chemically equivalent and which, when administered to the same individuals in the same dosage regimens, result in comparable bioavailabilities; (c) therapeutic equivalent nasal cannabinoid pharmaceutical compositions for nasal administration which, when administered to the same individuals in the same dosage regimens, provide essentially the same efficacy and/or toxicity; and (d) interchangeable nasal cannabinoid pharmaceutical compositions for nasal administration of the present invention which are pharmaceutically equivalent, bioequivalent and therapeutically equivalent.

While the intranasal nasal cannabinoid pharmaceutical compositions of the present invention are preferred pharmaceutical preparations when practicing the novel methods of the present invention, it should be understood that the novel topical intranasal cannabinoid pharmaceutical compositions and methods of the present invention also contemplate the pernasal administration of any suitable active ingredient, either alone or in combination with cannabinoid, mixtures of cannabinoids or other active ingredients, in any suitable semi-solid or viscous liquid nasal pharmaceutical preparation, such as a cream, a gel or an emulsion.

In accordance with the present invention, the viscosity of the novel nasal pharmaceutical compositions of the present invention is at least about 500 cps and may from range from between about 500 cps to about 100,000 cps prior to administration given associated thixotropic properties with some of the novel nasal pharmaceutical compositions. Preferably, the viscosity may range from between about 1000 cps and about 75,000 cps, more preferably between about 2500 cps and about 50,000 cps, and most preferably between about 5,000 cps and about 25,000 cps prior to administration or pump actuation, in view of thixotropic properties associated with some of the novel nasal pharmaceutical compositions.

In accordance with the present invention, in certain formulations the content of THC in the cannabinoid in the novel nasal pharmaceutical compositions of the present invention when treating indications such as pain, including pain caused by chronic pain, neuropathic pain, cancer and fibromyalgia, glaucoma, emesis, food intake, diabetes, liver disease, osteogenesis and cancer conditions relating to certain types of cancer including nausea and vomiting and the like or alleviating or reducing the symptoms associated therewith or caused thereby is at least about 0.1 mg of THC. Preferably, the THC content ranges from between about 0.1 mg and about 37.5 mg, more preferably between about 1 mg to about 20 mg, more preferably the THC content ranges between about 2 mg and about 10 mg, and most preferably the THC content ranges between about 0.5 mg and about 2.5 mg.

As to THC purity when for example treating indications such as pain, including pain caused by chronic pain, neuropathic pain, cancer and fibromyalgia, glaucoma, emesis, food intake, diabetes, liver disease, osteogenesis and cancer conditions relating to certain types of cancer including nausea and vomiting and the like or alleviating or reducing the symptoms associated therewith or caused thereby, the cannabinoid utilized to formulate the novel nasal pharmaceutical compositions of the present invention has a THC purity of preferably about 90%, more preferably a THC purity of about 95%, even more preferably a THC purity of about 98%, and even more preferably a THC purity of about 99%, and most preferably a THC purity of about 100% THC, otherwise pure THC. Thus, it should be understood that while the present invention contemplates a THC purity range when treating pain or alleviating or reducing pain symptoms caused by pain of from about 50% to about 100%, the most preferable THC purity range is between about 90% and about 100% and the most preferable THC purity range is about 100% THC.

In accordance with the present invention, in certain formulations the content of CBD in the cannabinoid in the novel nasal pharmaceutical compositions of the present invention, when treating indications such as epilepsy, schizophrenia, antipsychosis, anxiety, sleep disturbances, neurodegeneration, psychosis, depression, glaucoma, neurodegeneration, cerebral and myocardial ischemia, inflammation, immune responses, diabetes, liver disease, osteogenesis, a movement disorder, a mood disorder, a psychological disorder and Tourette syndrome or alleviating or reducing pain symptoms associated therewith or caused thereby, is at least about 0.1 mg of CBD. Preferably, the CBD content ranges from between about 0.1 mg to about 37.5 mg, more preferably between about 1 mg and about 35 mg, more preferably the CBD content ranges between about 2 mg to about 30 mg, and most preferably the CBD content ranges between about 5 mg and about 25 mg. Dosage amount particularly contemplated by the present invention include 20 mg and 37.5 mg of CBD.

As to CBD purity when, for example, when treating indications such as epilepsy, schizophrenia, antipsychosis, anxiety, sleep disturbances, neurodegeneration, psychosis, depression, glaucoma, neurodegeneration, cerebral and myocardial ischemia, inflammation, immune responses, diabetes, liver disease, osteogenesis, a movement disorder, a mood disorder, a psychological disorder and Tourette syndrome or alleviating or reducing pain symptoms associated therewith or caused thereby, the cannabinoid utilized to formulate the novel nasal pharmaceutical compositions of the present invention has a CBD purity of preferably about 50%, more preferably a BCD purity of about 60%, more preferably a BCD purity of about 70%, more preferably a BCD purity of about 80%, even more preferably a BCD purity of about 90%, about 95%, and about 98%, and about 99%, and even more preferably a CBD purity of about 99%, and most preferably a CBD purity of about 100% THC or otherwise pure CBD.

The present invention is also directed to packaged pharmaceuticals comprising the novel and improved nasal cannabinoid pharmaceutical compositions for topical administration into the nasal cavity of a subject. For example, the present invention contemplates pre-filled, single or multi-dose applicator systems for pernasal administration to strategically and uniquely deposit the nasal cannabinoid pharmaceutical compositions at the preferred locations within the nasal cavity for practicing the novel methods and teachings of the present invention.

Generally, speaking the applicator systems of the present invention are, e.g., airless fluid, dip-tube fluid dispensing systems or pumps or any other system suitable for practicing the methods of the present invention. The applicator systems or pumps include, for example, a chamber, pre-filled with multiple doses of an intranasal testosterone gel of the present invention, that is closed by an actuator nozzle. The actuator nozzle may comprise an outlet channel and tip, wherein the actuator nozzle is shaped to conform to the interior surface of a user's nostril for (a) consistent delivery of uniform dose amounts of an intranasal testosterone gel of the present invention during pernasal application within the nasal cavity, and (b) deposition at the instructed location within each nostril of a patient as contemplated by the novel methods and teachings of the present invention. Preferably, when inserted into a nasal cavity, the pump design is configured to help ensure that the nasal tip is properly positioned within the nasal cavity so that, when the gel is dispensed, the gel is dispensed within the appropriate location within the nasal cavity. See Steps 3 and 8 in FIG. 7A. See also FIG. 7B. Additionally, the nozzles to the pumps are preferably designed to dispense the gels from the side in a swirl direction, i.e., the tips of the nozzles are designed to dispense in a side distribution direction, as opposed to a direct distribution direction, onto the nasal mucosa, as shown in steps 4 and 9 of FIG. 7A. See also FIG. 7B. It is believed that the swirl action allows for better gel adhesion and side distribution from the nozzle tip avoids the dispensed gel from splashing back onto the tip. Finally, it is preferred to design the nozzle and tip to allow for any residual gel on the nozzle/tip to be wiped off as the tip is removed from the nasal cavity. See, e.g., FIGS. 7A and 7B.

Examples of pre-filled, multi-dose applicator systems include, e.g., (a) the COMOD system available from Ursatec, Verpackung-GmbH, Schillerstr. 4, 66606 St. Wendel, Germany, (b) the Albion or Digital airless applicator systems available from Airlessystems, RD 149 27380 Charleval, France or 250 North Route 303 Congers, N.Y. 10950, as shown in FIGS. 1-6, (c) the nasal applicators from Neopac, The Tube, Hoffmann Neopac AG, Burgdorfstrasse 22, Postfach, 3672 Oberdiessbach, Switzerland, or (d) the syringes for nasal delivery of the cannabinoid pharmaceutical compositions.

Preferably, the intranasal cannabinoid pharmaceutical compositions are filled into a preservative-free, airless multi-dose device able to accurately deliver doses of the above cannabinoid pharmaceutical composition, also at higher viscosities.

According to one aspect of the invention is provided a pharmaceutical composition of cannabinoid for nasal administration.

According to certain embodiments, the composition comprises: (1) a cannabinoid therapeutic active; (2) an oily vehicle; and (3) a wetting agent or mixture of wetting agents and/or a pharmaceutically acceptable surfactant or mixture of surfactants.

According to certain embodiments, the oily vehicle is one or more pharmaceutically acceptable Generally Recognized as Safe lipid.

According to certain embodiments, the oily vehicle is selected from the group consisting of: a pharmaceutically acceptable vegetable oil, a monoglyceride, a diglyceride, Sucrose acetate isobutyrate (SAIB), a synthetic triglyceride, and a combination thereof.

According to certain embodiments, the pharmaceutically acceptable vegetable oil is selected from the group consisting of: Almond Oil Sweet (*Prunus dulcis*), Almond Oil Virgin (*Prunus amygdalus*), Aloe Vera Oil (*Aloe barbadensis*), Apricot Kernel Oil (*Prunus armeniaca*), Argan Oil (*Argania spinosa*), Avocada Oil (*Persea americana*), Apricot Oil (*Prunus armeniaca*), Amla Oil (*Emblica officinalis*), Borage Oil (*Borago officinalis*), Black Seed Oil (*Nigella sativa*), Carrot Oil (*Daucus carota*), Coconut Oil (*Cocus nucifera*), Corn Oil, Cucumber Oil (*Cucumis sativa*), Chaulmogra Oil (*Hydnocarpus wightianus*), Emu Oil (*Dromaius novae-hollandiae*), Evening Primrose Oil (*Oenothera biennis*), Flaxseed Oil (*Linum usitatissimum*), Grapeseed Oil (*Vitus vinifera*), Hazel Nut Oil (*Avekkana*), Jojoba Oil Refined (*Simmondsia chinensis*), Moringa Oil (*Moringa oliefera*), Marula Oils (*Sclerocarya birrea*), Wheatgerm Oil, *Triticum vulgare*, Macadamia Oil, (*Macadamia ternifolia*), Musk Melon Oil (*Cuvumis melon*), Musk Oil (*Abelmoschus moschatus*), Mustered Oil, Neem Oil (*Azadirachta indica*), Olive Oil (*Olea europaea*), Peach Kernel Oil (*Prunus persica*), Peanut Oil (*Arachis hypogeae*), Pomegranate Oil, Punica granatum, Psoralea Oil (*Psoralea corylifolia*), Primrose Oil (*Oenothera bienni*), Papaya Seed Oil (*Carica papaya*), Rosehip Seed Oil (*Rosa rubiginosa*), Safflower Oil, Seasame Seed (Refined) (*Sesamum indicum*), Sea Buckthorn Oil (*Hippophae rhamnoides*), Soya Bean Oil (*Soja hispida*), Sunflower Oil (*Helianthus annus*), Sweet Almond Oil (*Prunus amygdalus* Var. Dulcus), Sweet Cherry Kernel Oil (*Prunus avium*), Walnut Oil (*Juglans regia*), Water Melon Oil (*Citrullus vulgaris*).

According to certain preferred embodiments, the oily vehicle comprises Castor Oil and/or sesame oil and/or SAIB.

According to certain embodiments, the cannabinoid therapeutic active, or mixture of actives, is selected from one or more of the group consisting of: tetrahydrocannabinol (THC), cannabidiol (CBD) or a mixture thereof, a prodrug of THC or CBD, a derivative of THC or CBD, and an analog of THC or CBD.

In certain embodiments, the cannabinoid therapeutic active is derived synthetically.

In certain embodiments, the cannabinoid therapeutic active or mixture of actives is obtained by extraction from a natural source such as a pure strain or blend of strains of *Cannabis sativa*.

According to certain embodiments, the a wetting agent or mixture of wetting agents and/or a pharmaceutically acceptable surfactant or mixture of surfactants is selected from the group consisting of: a polysorbate, a polyoxyethylene hydrogenated vegetable oil, a polyoxyethylene vegetable oil; a polyoxyethylene sorbitan fatty acid ester; a polyoxyethylene-polyoxypropylene block copolymer; a polyglycerol fatty acid ester; a polyoxyethylene glyceride; a polyoxyethylene sterol, or a derivative or analogue thereof; a reaction mixture of polyols and at least one member of the group consisting of fatty acids, glycerides, vegetable oils, hydrogenated vegetable oils, fractionated oils and sterols; a tocopheryl polyethylene glycol succinate; a sugar ester; a sugar ether; a sucroglyceride; an alkylglucoside; an alkylmaltoside; an alkylthioglucosides; a lauryl macrogolglyceride; a polyoxyethylene alkyl ether; a polyoxyethylene alkylphenol; a polyethylene glycol fatty acid ester; a polyethylene glycol glycerol fatty acid ester; a polyoxyethylene sorbitan fatty acid ester; a polyoxyethylene-polyoxypropylene block copolymer such as poloxamer-108, 188, 217, 238, 288, 338, 407, 124, 182, 183, 212, 331, or 335, or combinations thereof; an ionic hydrophilic surfactant such as sodium dodecyl sulphate or docusate sodium; a bile acid; a cholic acid; a deoxycholic acid; a chenodeoxycholic acid; salts thereof, and mixtures thereof.

According to certain embodiments, the composition further comprises a rheology modifying agent, for example, colloidal silica, silicates, alumina, a high molecular weight polymer or a solid/waxy substance, bee wax, alumina, silica, silicates and high melting waxes, and/or cetostearyl alcohol.

According to certain embodiments, the composition further comprises a mineral, an osmotic complement, a thickener, and/or a hydrophilic polymer.

According to certain embodiments, the hydrophilic polymer is selected from the group consisting of: HPMC, HPC, Sodium CMC, Sodium CMC and MCC, natural gums like Xanthan gum, Guar gum, gum acacia, gum tragacanth, starches like maize starch, potato starch, and pregelatinized starch.

According to certain embodiments, the surfactant is selected from the group consisting of: Glycol Distearate, Sorbitan Trioleate, Propylene Glycol Isostearate, Glycol Stearate, Sorbitan Sesquioleate, Lecithin, Sorbitan Oleate, Sorbitan Monostearate NF, Sorbitan Stearate, Sorbitan Isostearate, Steareth-2, Oleth-2, Glyceryl Laurate, Ceteth-2, PEG-30 Dipolyhydroxystearate, Glyceryl Stearate SE, Sorbitan Stearate (and) Sucrose Cocoate, PEG-4 Dilaurate, Methyl Glucose Sesquistearate, Lecithin HLB (variable) PEG-8 Dioleate, Sorbitan Laurate, Sorbitan Laurate, PEG-40 Sorbitan Peroleate, a polyoxyl glyceride, such as Labrafil® M1944CS, Laureth-4, PEG-7 Glyceryl Cocoate, PEG-20 Almond Glycerides, PEG-25 Hydrogenated Castor Oil, Stearamide MEA, Glyceryl Stearate (and) PEG-100 Stearate, Polysorbate 85, PEG-7 Olivate, Cetearyl Glucoside, Stearamide MEA, PEG-8 Oleate, Polyglyceryl-3 Methylglucose Distearate, Oleth-10, Oleth-10/Polyoxyl 10 Oleyl Ether NF, Ceteth-10, PEG-8 Laurate, Cocamide MEA, Polysorbate 60 NF, Polysorbate 60, Polysorbate 80, Isosteareth-20, PEG-60 Almond Glycerides, PEG-20 Methyl Glucose Sesquistearate, Ceteareth-20, Oleth-20, Steareth-20, Steareth-20, Steareth-21, Steareth-21, Ceteth-20, and Steareth-100.

According to certain preferred embodiments, the cannabinoid therapeutic active is CBD, the oily vehicle is Castor Oil, and the wetting agent is Oleoyl Polyoxylglycerides.

According to certain preferred embodiments, the cannabinoid therapeutic active is THC, the oily vehicle is Castor Oil, and the wetting agent is Oleoyl Polyoxylglycerides.

According to certain preferred embodiments, the cannabinoid therapeutic active is a mixture comprising THC and CBD, the oily vehicle is Castor Oil, and the wetting agent is Oleoyl Polyoxylglycerides.

According to certain embodiments, the cannabinoid therapeutic active is a mixture comprising THC and CBD, wherein the ratio of THC:CBD is between about 0.1:99.9 and about 99.9:0.1, preferably between 95:5 and about 75:25 (THC-rich), between 60:40 and 40:60 (approx. 1:1) and between 1:99 and 25:75 (CBD-rich). Thus, when using CBD-rich in combination with THC, the ratio contemplated in accordance with the present invention is 0-100:25-75. The use of pure synthetic CBD or THC as contemplated by the present invention includes greater than about 95%, greater than about 98% or even 100%. Thus, the present invention contemplates use of both, herbal extract mixtures (with their corresponding terpenes) or synthetically pure compounds. Cannababinoid products are regulated by Medical Marijuana legislation, while pure synthetics follow the traditional FDA-Health Canada clinical development pathway.

According to certain embodiments, the cannabinoid therapeutic active or mixture of actives is about 10% w/w, the Castor Oil is about 82% w/w, and the Oleoyl Polyoxylglycerides are about 4% w/w of the composition. In certain preferred embodiments, the composition further comprises Silicon Dioxide.

In certain embodiments, the cannabinoid therapeutic active or mixture of actives is about 10% w/w, the Sesame Oil is about 86% w/w, the Oleoyl Polyoxylglycerides are about 2% w/w of the composition, and the Silicon Dioxide is about 2% w/w of the composition.

In certain embodiments, the cannabinoid therapeutic active or mixture of actives is about 20% w/w, the Castor Oil is about 73.4% w/w, the Oleoyl Polyoxylglycerides are about 3.3% w/w, and the Silicon Dioxide is about 3.3% w/w of the composition.

In certain embodiments, the cannabinoid therapeutic active is cannabinoid therapeutic active or mixture of actives, the oily vehicle is sesame oil, the wetting agent is Oleoyl Polyoxylglycerides, and the rheology modifying agent is Silicon Dioxide.

In certain embodiments, the cannabinoid therapeutic active or mixture of actives is about 10% w/w, the Castor oil is about 86% w/w, the Oleoyl Polyoxylglycerides are about 2% w/w, and the Silicon Dioxide is about 2% w/w of the composition.

In certain embodiments, the cannabinoid therapeutic active or mixture of actives is about 20% w/w, the sesame oil is about 73.4% w/w, the Oleoyl Polyoxylglycerides are about 3.3% w/w, and the Silicon Dioxide is about 3.3% w/w of the composition.

In certain embodiments, the cannabinoid therapeutic active is cannabinoid therapeutic active or mixture of actives, the oily vehicle is sesame oil and olive oil, the wetting agent is Oleoyl Polyoxylglycerides, and the rheology modifying agent is Hydroxypropylcellulose.

In certain embodiments, the cannabinoid therapeutic active or mixture of actives is about 12% w/w, the sesame oil is about 20% w/w, the olive oil is about 20% w/w, the Oleoyl Polyoxylglycerides are about 4% w/w, the Hydroxypropylcellulose is about 4% w/w, further comprising about 40% w/w water.

In certain embodiments, the composition comprises cannabinoid therapeutic active or mixture of actives and SAIB. For example, the composition may consist essentially of cannabinoid therapeutic active or mixture of actives and SAIB.

In certain embodiments, the composition comprises about 10% w/w cannabinoid therapeutic active or mixture of actives.

In certain embodiments, the cannabinoid therapeutic active is cannabinoid therapeutic active or mixture of actives, the oily vehicle is SAIB and medium chain triglycerides, and the wetting agent is Polyoxyl 35 Hydrogenated Castor Oil.

In certain embodiments, the cannabinoid therapeutic active or mixture of actives is about 10% w/w, the SAIB is about 50% w/w, the medium chain triglycerides are about 35% w/w, and the Polyoxyl 35 Hydrogenated Castor Oil is about 5% w/w.

In certain embodiments, the cannabinoid therapeutic active is cannabinoid therapeutic active or mixture of actives, the oily vehicle is SAIB and medium chain triglycerides, and the wetting agent is Oleoyl Polyoxylglycerides.

In certain embodiments, the cannabinoid therapeutic active or mixture of actives is about 20% w/w, the SAIB is about 44.5% w/w, the medium chain triglycerides are about 31% w/w, and the Oleoyl Polyoxylglycerides are about 4.5% w/w.

According to a further aspect of the invention is provided a composition capable of achieving a serum cannabinoid therapeutic active or mixture of actives concentration of from at least about 0.5 ng/ml before about 8 hours after a single administration, such as from at least about 0.5 ng/ml to about 40 ng/ml within 8 h after a single administration in one or both nasal vestibules of the nostrils of a fasted subject.

According to a further aspect of the invention is provided a composition capable of achieving a serum cannabinoid therapeutic active or mixture of actives concentration of >40 ng/ml within 8 h after a single administration in one or both nasal vestibules of the nostrils of a fasted subject a fasted subject.

According to a further aspect of the invention is provided a composition capable of achieving a serum cannabinoid therapeutic active or mixture of actives concentration of >30 ng/ml within 8 h after a single administration in one or both nasal vestibules of the nostrils of a fasted subject a fasted subject.

According to a further aspect of the invention is provided a composition capable of achieving a serum cannabinoid therapeutic active or mixture of actives concentration of >25 ng/ml within 8 h after a single administration in one or both nasal vestibules of the nostrils of a fasted subject a fasted subject.

According to a further aspect of the invention is provided a composition capable of achieving a serum cannabinoid therapeutic active or mixture of actives concentration of >20 ng/ml within 8 h after a single administration in one or both nasal vestibules of the nostrils of a fasted subject a fasted subject.

According to a further aspect of the invention is provided a composition capable of achieving a serum cannabinoid therapeutic active or mixture of actives concentration of >10 ng/ml within 8 h after a single administration in one or both nasal vestibules of the nostrils of a fasted subject a fasted subject.

According to a further aspect of the invention is provided a composition capable of achieving a serum cannabinoid therapeutic active or mixture of actives concentration of >1 ng/ml within 8 h after a single administration in one or both nasal vestibules or nostrils of a fasted subject a fasted subject.

According to a further aspect of the invention is provided a composition capable of achieving a serum cannabinoid therapeutic active or mixture of actives concentration of at least about 0.5 ng/ml within 8 h after a single nasal administration in one or both nasal vestibules or nostrils of a fasted subject a fasted subject.

According to a further aspect of the invention is provided a composition capable of achieving a serum cannabinoid therapeutic active or mixture of actives concentration of >0.1 ng/ml within 8 h after nasal administration in one or both nasal vestibules or nostrils of a fasted subject a fasted subject.

According to a further aspect of the present invention is provided the use of a dispenser to administer cannabinoid therapeutic active or mixture of actives compositions as herein described to the nasal vestibule or nostril of patients in need thereof.

According to a further aspect of the present invention is provided the use of an airless dispenser to administer cannabinoid therapeutic active or mixture of actives compositions as herein described to the nasal vestibule of patients to patients in need thereof.

According to a further embodiment of the present invention is provided the use of an airless metered-dose dispenser to administer cannabinoid therapeutic active or mixture of actives compositions as herein described to the nasal vestibule of patients to patients in need thereof.

According to a further aspect of the present invention is provided a use of an airless metered-dose dispenser to administer cannabinoid therapeutic active or mixture of actives compositions as herein described to the nasal vestibule of patients to patients in need thereof.

According to a further aspect of the present invention is provided the use of an airless metered-dose dispenser to administer a dose per nostril in an amount of between about 50 and about 150 µL of a cannabinoid therapeutic active or mixture of actives gel composition as herein described to a nasal vestibule of a patient in need thereof.

According to a further aspect of the present invention is provided the use of an airless metered-dose dispenser to administer from about 0.1 to about 75 mg of cannabinoid therapeutic active or mixture of actives comprised in a gel composition to the nasal vestibule of patients to patients in need thereof.

According to a further aspect of the present invention is the use of an airless metered-dose dispenser to administer from about 0.1 to about 75 mg of cannabinoid therapeutic active or mixture of actives dissolved in a gel composition, as herein described to the nasal vestibule of patients to patients in need thereof.

According to a further aspect of the present invention is provided the use of an airless metered-dose dispenser to administer a dose per nostril in an amount of between about 50 and about 150 µL of a cannabinoid therapeutic active or mixture of actives gel composition, wherein each nasal dose contains from between about 0.1 and about 37.5 mg of cannabinoid therapeutic active or mixture of actives, as herein described to the nasal vestibule of patients to patients in need thereof. In other words, about 0.1% for a 50 µL dose=0.5 mg (lowest dose volume) to about 25% for a 150 µL dose=37.5 mg (highest dose volume), when applied the dose is applied to one nostril as a single dose. However, when the dose is applied to each nostril, the total dose amount administered doubles and will range from about 0.2 mg to about 75 mg (or from about 0.1 mg/per each nostril to about 37.5 mg/per each nostril).

According to a further aspect of the present invention is provided a nasal administration of a cannabinoid therapeutic active or mixture of actives composition as herein described for the treatment of antipsychosis, epilepsy, anxiety, sleep disturbances, neurodegeneration, psychosis, depression, glaucoma, neurodegeneration, cerebral and myocardial ischemia, inflammation, pain including chronic pain, immune responses, emesis, food intake, such as appetite stimulation in HIV/AIDS, type-1 diabetes, liver disease, osteogenesis, cancer, conditions relating to certain types of cancer including nausea and vomiting, a movement disorder, a mood disorder, a psychological disorder and Tourette syndrome.

According to a further aspect of the present invention is provided a nasal administration of a cannabinoid therapeutic active or mixture of actives composition as herein described for the treatment of schizophrenia, pain, including chronic pain, migraine, spasticity, epilepsy or anxiety.

According to a further aspect of the present invention are provided nasal semi-solid or viscous liquid pharmaceutical compositions, namely, creams, gels and emulsions, preferably thixotropic creams, gels and emulsions, of which each is formulated with a therapeutically effective amount of cannabinoid for topical administration into one or more nasal vestibules or nostrils of a subject to treat a subject for a disease state, or to alleviate or mitigate symptoms thereof, that is treatable with cannabinoid.

In certain embodiments contemplated by the present invention, the nasal cannabinoid composition is a nasal gel composition, preferably a thixotropic nasal gel composition, formulated with a therapeutically effective amount of cannabinoid for topical application into one or both nasal vestibules of the nostrils of a subject.

It should be understood by those versed in this art that the amount of cannabinoid, including mixtures thereof, in a nasal cannabinoid pharmaceutical composition of the present invention that will be therapeutically effective in a specific situation will depend upon such things as the type of cannabinoid utilized, the dosing regimen selected, the application site, the particular composition, dose longevity and the cannabinoid condition being treated. As such, it is generally not practical to identify specific administration amounts herein; however, it is believed that those skilled in the art will be able to determine appropriate therapeutically effective amounts based on the guidance provided herein, information available in the art pertaining to cannabinoid therapy, and routine testing.

It should be further understood that the above summary of the present invention is not intended to describe each disclosed embodiment or every implementation of the present invention. The description further exemplifies illustrative embodiments. In several places throughout the specification, guidance is provided through examples, which examples can be used in various combinations. In each instance, the examples serve only as representative groups and should not be interpreted as exclusive examples.

BRIEF DESCRIPTION OF THE DRAWINGS

The foregoing and other objects, advantages and features of the present invention, and the manner in which the same are accomplished, will become more readily apparent upon consideration of the following detailed description of the invention taken in conjunction with the accompanying figures and examples, which illustrate embodiments, wherein:

FIGS. 7A and 7B illustrate use of a multiple dose dispenser in accordance with the present invention;

DESCRIPTION OF THE INVENTION

Figure 1:
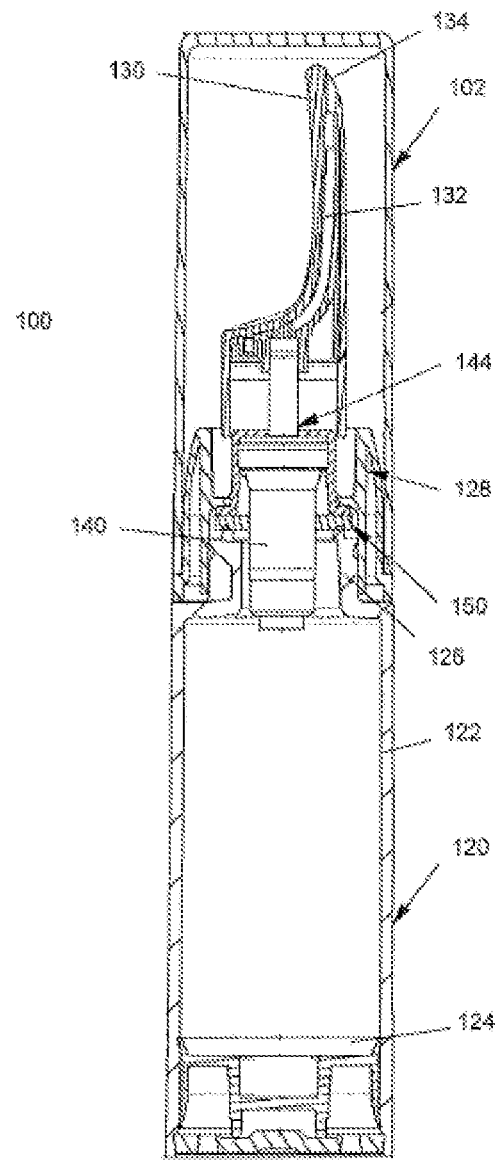
FIG. 1 is a side view of a first embodiment of a distributor pump of the invention.

By way of illustrating and providing a more complete appreciation of the present invention and many of the attendant advantages thereof, the following detailed description and examples are given concerning the novel lower dosage strength intranasal nasal cannabinoid pharmaceutical compositions, application devices and methods of the present invention.

Definitions

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein, "at least one" is intended to mean "one or more" of the listed elements.

Singular word forms are intended to include plural word forms and are likewise used herein interchangeably where appropriate and fall within each meaning, unless expressly stated otherwise.

Except where noted otherwise, capitalized and non-capitalized forms of all terms fall within each meaning.

Unless otherwise indicated, it is to be understood that all numbers expressing quantities, ratios, and numerical properties of ingredients, reaction conditions, and so forth used in the specification and claims are contemplated to be able to be modified in all instances by the term "about".

All parts, percentages, ratios, etc. herein are by weight unless indicated otherwise.

As used herein, "bioequivalence" or "bioequivalent", refers to nasally administered nasal cannabinoid pharmaceutical compositions or drug products which are pharmaceutically equivalent and their bioavailabilities (rate and extent of absorption) after administration in the same molar dosage or amount are similar to such a degree that their therapeutic effects, as to safety and efficacy, are essentially the same. In other words, bioequivalence or bioequivalent means the absence of a significant difference in the rate and extent to which cannabinoid becomes available from such compositions at the site of cannabinoid action when administered at the same molar dose under similar conditions, e.g., the rate at which cannabinoid can leave such a composition and the rate at which cannabinoid can be absorbed and/or become available at the site of action to affect the disorder. In other words, there is a high degree of similarity in the bioavailabilities of two cannabinoid gel composition pharmaceutical products for nasal administration (of the same galenic form) from the same molar dose, that are unlikely to produce clinically relevant differences in therapeutic effects, or adverse reactions, or both. The terms "bioequivalence", as well as "pharmaceutical equivalence" and "therapeutic equivalence" are also used herein as defined and/or used by (a) the FDA, (b) the Code of Federal Regulations ("C.F.R."), Title 21, (c) Health Canada, (d) European Medicines Agency (EMEA), and/or (e) the Japanese Ministry of Health and Welfare. Thus, it should be understood that the present invention contemplates cannabinoid nasal compositions for nasal administration or drug products that may be bioequivalent to other cannabinoid nasal compositions for nasal administration or drug products of the present invention. By way of example, a first cannabinoid nasal composition for nasal administration or drug product is bioequivalent to a second cannabinoid nasal composition for nasal administration or drug product, in accordance with the present invention, when the measurement of at least one pharmacokinetic parameter(s), such as a Cmax, Tmax, AUC, etc., of the first cannabinoid nasal composition for nasal administration or drug product varies by no more than about ±25%, when compared to the measurement of the same pharmacokinetic parameter for the second cannabinoid nasal composition for nasal administration or drug product of the present invention.

As used herein, "bioavailability" or "bioavailable", means generally the rate and extent of absorption of cannabinoid into the systemic circulation and, more specifically, the rate or measurements intended to reflect the rate and extent to which cannabinoid becomes available at the site of action or is absorbed from a drug product and becomes available at the site of action. In other words, and by way of example, the extent and rate of cannabinoid absorption from a nasal pharmaceutical composition for nasal administration of the present invention as reflected by a time-concentration curve of cannabinoid in systemic circulation.

As used herein, the terms "pharmaceutical equivalence" or "pharmaceutically equivalent", refer to cannabinoid nasal compositions for nasal administration or drug products of the present invention that contain the same amount of cannabinoid, in the same dosage forms, but not necessarily containing the same inactive ingredients, for the same route of administration and meeting the same or comparable compendial or other applicable standards of identity, strength, quality, and purity, including potency and, where applicable, content uniformity and/or stability. Thus, it should be understood that the present invention contemplates cannabinoid nasal compositions for nasal administration or drug products that may be pharmaceutically equivalent to other cannabinoid nasal compositions for nasal administration or drug products used in accordance with the present invention.

As used herein, "therapeutic equivalence" or "therapeutically equivalent", means those cannabinoid nasal compositions for nasal administration or drug products which (a) will produce the same clinical effect and safety profile when utilizing cannabinoid drug product to treat a cannabinoid treatable disorder in accordance with the present invention and (b) are pharmaceutical equivalents, e.g., they contain cannabinoid in the same dosage form, they have the same route of administration; and they have the same cannabinoid strength. In other words, therapeutic equivalence means that a chemical equivalent of a cannabinoid nasal composition of the present invention (i.e., containing the same amount of cannabinoid in the same dosage form when administered to the same individuals in the same dosage regimen) will provide essentially the same efficacy and toxicity.

As used herein, "plasma cannabinoid level" means the level of cannabinoid in the plasma of a subject. The plasma cannabinoid level is determined by methods known in the art.

"Diagnosis" or "prognosis," as used herein, refers to the use of information (e.g., biological or chemical information from biological samples, signs and symptoms, physical exam findings, psychological exam findings, etc.) to anticipate the most likely outcomes, timeframes, and/or responses to a particular treatment for a given disease, disorder, or condition, based on comparisons with a plurality of individuals sharing symptoms, signs, family histories, or other data relevant to consideration of a patient's health status, or the confirmation of a subject's affliction.

A "subject" according to some embodiments is an individual whose signs and symptoms, physical exams findings and/or psychological exam findings are to be determined and recorded in conjunction with the individual's condition (i.e., disease or disorder status) and/or response to a candidate drug or treatment.

"Subject," as used herein, is preferably, but not necessarily limited to, a human subject. The subject may be male or female, and may be of any race or ethnicity, including, but not limited to, Caucasian, African-American, African, Asian, Hispanic, Indian, etc. Subject as used herein may also include an animal, particularly a mammal such as a canine, feline, bovine, caprine, equine, ovine, porcine, rodent (e.g., a rat and mouse), a lagomorph, a primate (including non-human primate), etc., that may be treated in accordance with the methods of the present invention or screened for veterinary medicine or pharmaceutical drug development purposes. A subject according to some embodiments of the present invention include a patient, human or otherwise, in need of therapeutic treatment for a disorder treatable with cannabinoid.

"Treatment," as used herein, includes any drug, drug product, method, procedure, lifestyle change, or other adjustment introduced in attempt to effect a change in a particular aspect of a subject's health (i.e., directed to a particular disease, disorder, or condition) or alleviate or mitigate symptoms of a particular disease, disorder or condition.

"Drug" or "drug substance," as used herein, refers to an active ingredient, such as a chemical entity or biological entity, or combinations of chemical entities and/or biological entities, suitable to be administered to a subject to (a) treat anorgasmia and/or (b) treat HSDD. In accordance with the present invention, the drug or drug substance is cannabinoid, such as therapeutic CBD or THC or mixtures thereof.

The term "drug product," as used herein, is synonymous with the terms "medicine," "medicament," "therapeutic intervention," "pharmaceutical product or "pharmaceutical composition." Most preferably, a drug product is approved by a government agency for use in accordance with the methods of the present invention. A drug product, in accordance with the present invention, is an intranasal pharmaceutical composition or composition formulated with a drug substance, i.e., a cannabinoid, such as CBD and THC and mixtures thereof.

"Disease," "disorder," and "condition" are commonly recognized in the art and designate the presence of signs and/or symptoms in an individual or patient that are generally recognized as abnormal and/or undesirable. Diseases or conditions may be diagnosed and categorized based on pathological changes. The disease or condition may be selected from the types of diseases listed in standard texts, such as Harrison's Principles of Internal Medicine, 1997, or Robbins Pathologic Basis of Disease, 1998.

As used herein, "diagnosing" or "identifying a patient or subject having a disorder treatable with a cannabinoid" refers to a process of determining if an individual is afflicted with a disorder treatable with a cannabinoid.

The present invention provides a non-oral, non-injectable form of cannabinoids, for example, THC, CBD and mixtures, which is convenient and can be self-administered. The composition can be administered by a care-giver if needed, is relatively stable, is readily absorbed after administration comparatively to other available forms, has good bioavailability, is believed to avoid or at least have reduced first pass metabolism, and is able to achieve desired levels of cannabinoids in the bloodstream. The therapeutic is formulated for nasal delivery, by administration to, and absorption through, the mucosa of the nasal cavity.

Until the present, it is believed that semi-solid or viscous liquid pharmaceutical compositions of cannabinoids, namely, cannabinoid gels, creams or emulsion, for topical application into the nasal cavity of humans have been unknown. Cannabinoids are substances with a high octanol-water partition coefficient (log P>5), that will dissolve in organic solvents, such as toluene, dichloromethane acetone, ethanol, etc., in natural vegetable oils, such as sesame oil, Castor Oil, olive oil and similar, and in synthetic resins and waxy materials, such as sucrose acetate isobutyrate.

In accordance with the present invention, and generally speaking a therapeutically effective, nasally administered semi-solid or viscous liquid composition of cannabinoids, such as a gel, a cream or an emulsion, preferably a thixotropic gel, cream or an emulsion, can be formulated comprising cannabinoid therapeutic active or mixture of actives and a pharmaceutically acceptable vehicle.

In one aspect of the present invention, a therapeutically effective, nasally administered gel composition of cannabinoids can be formulated comprising the following three ingredients:
  (1) The cannabinoid therapeutic active or mixture of actives;
  (2) An oily vehicle selected from any one or mixture of lipids. Preferably, lipids Generally Recognized as Safe (GRAS) are used. More preferably, the lipids are common, natural, GRAS lipids. Preferably, the lipids should also be pharmaceutically acceptable.
  (3) A wetting agent or mixture of wetting agents, and/or a pharmaceutically acceptable surfactant or mixture of surfactants.

Optionally, a rheology modifying agent can additionally be used in the composition.

Optionally, the oily composition may be emulsified into an aqueous phase to form an emulsion or cream.

The therapeutic active is preferably THC or CBD, but may also be prodrugs, derivatives, or analogs of THC or CBD, or a combination of these. In accordance with the present invention, when THC and CBD are used in combination, the ratio of THC:CBD contemplated is between about 0.1:99.9 and about 99.9:0.1, preferably between 95:5 and about 75:25, more preferably between 1:1, and most preferably between 60:40 and 40:60. When using CBD-rich in combination with THC, the ratio contemplated in accordance with the present invention is 0-100:25-75. The use of pure synthetic CBD or THC as contemplated by the present invention includes greater than about 95%, greater than about 98% or even 100%. Thus, the present invention contemplates use of herbal extract mixtures (with their corresponding terpenes) derived from plant sources, may or may not contain traces of other cannabinoids or natural products, or they may be derived after at least 1 synthetic chemistry step. It would be understood to a person of skill in the art that other cannabinoids may also be used to form the composition, though they may have therapeutic properties different from those of the CBD-based compositions, and that cannabinoid products are regulated by Medical Marijuana legislation, while pure synthetics follow the traditional FDA-Health Canada clinical development pathway. In preferable embodiments, the therapeutic active comprises about 0.1-40% by weight of the total composition, preferably about 5-30% by weight of the total composition, most preferably about 15-30% by weight of the total composition.

The oily vehicle may be, for example, any pharmaceutically acceptable vegetable oil, monoglycerides, diglycerides, synthetic triglycerides, Almond Oil Sweet (*Prunus dulcis*), Almond Oil Virgin (*Prunus amygdalus*), Aloe Vera Oil (*Aloe barbadensis*), Apricot Kernel Oil (*Prunus armeniaca*), Argan Oil (*Argania spinosa*), Avocado Oil (*Persea americana*), Apricot Oil (*Prunus armeniaca*), Amla Oil (*Emblica officinalis*), Borage Oil (*Borago officinalis*), Black Seed Oil (*Nigella sativa*), Carrot Oil (*Daucus carota*), Coconut Oil (*Cocus nucifera*), Corn Oil, Cucumber Oil (*Cucumis sativa*), Chaulmogra Oil (*Hydnocarpus wightianus*), Emu Oil (*Dromaius novae-hollandiae*), Evening Primrose Oil (*Oenothera biennis*), Flaxseed Oil (*Linum usitatissimum*), Grapeseed Oil (*Vitus vinifera*), Hazel Nut Oil (*Avekkana*), Jojoba Oil Refined (*Simmondsia chinensis*), Moringa Oil (*Moringa oliefera*), Marula Oils (*Sclerocarya birrea*), Wheatgerm Oil, *Triticum vulgare*, Macadamia Oil, (*Macadamia ternifolia*), Musk Melon Oil (*Cuvumis melon*), Musk Oil (*Abelmoschus moschatus*), Mustered Oil, Neem Oil (*Azadirachta indica*), Olive Oil (*Olea europaea*), Peach Kernel Oil (*Prunus persica*), Peanut Oil (*Arachis hypogeae*), Pomegranate Oil, Punica granatum, Psoralea Oil (*Psoralea corylifolia*), Primrose Oil (*Oenothera bienni*), Papaya Seed Oil (*Carica papaya*), Rosehip Seed Oil (*Rosa rubiginosa*), Safflower Oil, Seasame Seed (Refined) (*Sesamum indicum*), Sea Buckthorn Oil (*Hippophae rhamnoides*), Soya Bean Oil (*Soja hispida*), Sunflower Oil (*Helianthus annus*), Sweet Almond Oil (*Prunus amygdalus* Var. Dulcus), Sweet Cherry Kernel Oil (*Prunus avium*), Walnut Oil (*Juglans regia*), Water Melon Oil (*Citrullus vulgaris*). Sucrose acetate isobutyrate (SAIB) was also found to be an acceptable vehicle, as were mixtures of oils or mixtures of oils with SAIB.

In preferable embodiments, the oily or emulsified vehicle comprises about 3%-99%, by weight, of the total composition.

The wetting agent or mixture of wetting agents, and/or a pharmaceutically acceptable surfactant or mixture of surfactants may be, for example, a polysorbate, a polyoxyethylene hydrogenated vegetable oil, a polyoxyethylene vegetable oil; a polyoxyethylene sorbitan fatty acid ester; a polyoxyethylene-polyoxypropylene block copolymer; a polyglycerol fatty acid ester; a polyoxyethylene glyceride; a polyoxyethylene sterol, or a derivative or analogue thereof; a reaction mixture of polyols and at least one member of the group consisting of fatty acids, glycerides, vegetable oils, hydrogenated vegetable oils, fractionated oils and sterols; a tocopheryl polyethylene glycol succinate; a sugar ester; a sugar ether; a sucroglyceride; an alkylglucoside; an alkylmaltoside; an alkylthioglucosides; a lauryl macrogolglyceride; a polyoxyethylene alkyl ether; a polyoxyethylene alkylphenol; a polyethylene glycol fatty acid ester; a polyethylene glycol glycerol fatty acid ester; a polyoxyethylene sorbitan fatty acid ester; a polyoxyethylene-polyoxypropylene block copolymer such as poloxamer-108, 188, 217, 238, 288, 338, 407, 124, 182, 183, 212, 331, or 335, or combinations thereof; an ionic hydrophilic surfactant such as sodium dodecyl sulphate or docusate sodium; a bile acid; a cholic acid; a deoxycholic acid; a chenodeoxycholic acid; salts thereof, and mixtures thereof.

In preferable embodiments, the wetting agent comprises about 0.1%-10%, by weight, of the total composition.

The rheology modifying agent, for example, a thickener, may be, for example, colloidal silica, silicates, alumina, or a high molecular weight polymer or a solid/waxy substance, which may be added to obtain the desired rheology. Examples of thickeners include any one or mixture of the following substances: bee wax, alumina, silica, silicates and high melting waxes and surfactants like cetostearyl alcohol. Ranges for incorporation into the composition those that increase the viscosity to a preferable minimum of about 500 cPs, a preferable maximum of about 30,000 cPs, and preferably into a range of 1000-10,000 cPs for rapid and convenient administration. Too fluid and the liquid will drain from the nose, and too viscous and the product cannot be administered easily with a small metered dose pump. The optimal viscosity for oily gels for use in devices such as Aptar Albion 15 manually actuated pump device is in the range of 1000-5000 cPs.

When used, typically, the rheology modifying agent comprises no more than about 10%, by weight, of the total composition.

Optionally, the composition can be dispersed or emulsified in an aqueous phase wherein the lipid and aqueous phases are mixed until homogeneous to form a cream (o/w or w/o creams) or emulgel or multiple emulsions (o/w/o or w/o/w) type product like topical mixture. The aqueous phase in such compositions can make up 10-90% (by weight) of the total composition, the remaining being a lipid vehicle composition as described above. The aqueous phase optionally may contain minerals, osmotic complements and thickeners. Hydrophilic polymers can be used to gel the aqueous phase if required. The non-limiting examples of these include HPMC, HPC, Sodium CMC, Sodium CMC and MCC, natural gums like Xanthan gum, Guar gum, gum acacia, gum tragacanth, starches like maize starch, potato starch, pregelatinized starch etc. The viscosity of aqueous based product can be higher compared to oily gels.

For emulsification of oil into water or vice versa any single or combination of surfactants can be used. Examples of surfactants include any one or mixture of surfactants. The surfactants may belong to non-ionic, anionic or cationic surfactants: Glycol Distearate, Sorbitan Trioleate, Propylene Glycol Isostearate, Glycol Stearate, Sorbitan Sesquioleate, Lecithin, Sorbitan Oleate, Sorbitan Monostearate NF, Sorbitan Stearate, Sorbitan Isostearate, Steareth-2, Oleth-2, Glyceryl Laurate, Ceteth-2, PEG-30 Dipolyhydroxystearate, Glyceryl Stearate SE, Sorbitan Stearate (and) Sucrose Cocoate, PEG-4 Dilaurate, Methyl Glucose Sesquistearate, Lecithin HLB (variable) PEG-8 Dioleate, Sorbitan Laurate, Sorbitan Laurate, PEG-40 Sorbitan Peroleate, a polyoxyl glyceride, such as Labrafil® M1944CS, Laureth-4, PEG-7 Glyceryl Cocoate, PEG-20 Almond Glycerides, PEG-25 Hydrogenated Castor Oil, Stearamide MEA, Glyceryl Stearate (and) PEG-100 Stearate, Polysorbate 85, PEG-7 Olivate, Cetearyl Glucoside, Stearamide MEA, PEG-8 Oleate, Polyglyceryl-3 Methyglucose Distearate, Oleth-10, Oleth-10/Polyoxyl 10 Oleyl Ether NF, Ceteth-10, PEG-8 Laurate, Cocamide MEA, Polysorbate 60 NF, Polysorbate 60, Polysorbate 80, Isosteareth-20, PEG-60 Almond Glycerides, PEG-20 Methyl Glucose Sesquistearate, Ceteareth-20, Oleth-20, Steareth-20, Steareth-20, Steareth-21, Steareth-21, Ceteth-20, Steareth-100. Ranges for incorporation into the composition are those that allow for the spreading of the gel upon the nasal mucosa and that allow absorption of the medication through the nasal tissues and into the bloodstream, 0.001-20%, preferably 1-10% or 1-5% (by weight).

Viscous oily, emulsions or creams compositions of the invention can be administered by finger, syringe, single use blow-fill-seal devices, airless pump devices and other alternatives. Emulsions may also be delivered via sprays, as well as methods already described, depending on the consistency of the composition. The container from which gel is applied may be a tube, a jar, an applicator, etc., and the container may be single-dose or may be a multidose device. The single dose container and applicator may be in the form of ampule made from soft gelatine. The delivery device may be disposable or reusable.

A metered dose pump delivery device can be used to deliver exact quantities of the drug substance to the patient. For example, a multi-dose device that allows delivery of precise dosage amounts to the external wall of one or both nostrils of the middle-upper nasal cavity (under cartilage)

may be used for depositing the dosage thereon. Once the drug substance is administered onto the external wall of the nasal cavity of a nostril, the outer nose is preferably gently massaged with fingers to evenly distribute the drug substance throughout the nasal cavity with minimal or no dosage loss into the throat or outside the nose. Examples of multi-dose devices for pernasal deposition at the preferred location within the nose in accordance with the present invention include the COMOD system available from Ursatec, Verpackung-GmbH, Schillerstr. 4, 66606 St. Wendel, Germany, or the Albion or Digital airless applicator systems available from Airless systems, RD 149 27380 Varleval, France or 250 North Route 303 Congers, N.Y. 10950. Such nasal multi-dose dispenser devices may be further adapted for an airless fluid dispensing system, or for a dip tube fluid dispensing system.

Preferably, the dose administered is in the range of between about 0.1 mg and about 75 mg of cannabinoid (total) or up to about 37.5 mg per single application per nostril.

The delivery device or container is single-use or multi-use and is devised to avoid contact of the product with air during storage and use.

The oily gel, emulsion or cream can be applied in the nose approximately 1 inch inside the opening (nostril) using a dispenser tip appropriately designed and safe to reach up into the nose and attached to a container. The tip preferably has rounded edges to avoid injury. The nose is then massaged to spread the composition to a thin film inside the nostril which will assist in absorption of the active ingredient into the mucosal tissues.

Oily gel emulsion and cream compositions may be abuse deterrent or have low abuse liability.

Food effects are often observed when a fat-soluble drug is administered orally. Food effects may also be observed when there is a high concentration of lipids in the bloodstream (LDL, HDL etc.).

The compositions according to the present invention can be used as medical *cannabis* to treat a number of conditions. The following list is representative of conditions treatable by either one or another of the cannabinoids and is not meant to be exclusive or exhaustive: antipsychosis, epilepsy, anxiety, sleep disturbances, neurodegeneration, psychosis, depression, glaucoma, neurodegeneration, cerebral and myocardial ischemia, inflammation, pain including chronic pain, immune responses, emesis, food intake, such as appetite stimulation in HIV/AIDS, type-1 diabetes, liver disease, osteogenesis, cancer, conditions relating to certain types of cancer including nausea and vomiting, a movement disorder, a mood disorder, a psychological disorder and Tourette syndrome. See, e.g.: Whiting P. F. et al.: Cannabinoids for Medical Use: A Systematic Review and Meta-analysis. *JAMA.* 2015 Jun. 23-30; 313(24):2456-73. doi: 10.1001/jama.2015.6358; Grotenhermen, F. et al.: The Therapeutic Potential of *Cannabis* and Cannabinoids. *Dtsch Arztebl Int.* 2012 July; 109(29-30): 495-501, Published online 2012 Jul. 23. doi: 10.3238/arztebl.2012.0495; Bertha K. Madras: Update of *Cannabis* and its medical use. 37th ECDD (2015) Agenda item 6.2 available at http://www.who.int/medicines/access/controlled-substances/6_2_cannabis_up-date.pdf; Drug Facts, Marijuana as Medicine. National Institutes of Drug Abuse, Revised April, 2017, available at https://www.drugabuse.gov/publications/drugfacts/marijuana-medicine and https://d14rmgtrwzf5a.cloudfront.net/sites/default/files/df_mj_medicine_a-pril2017.pdf; and 10 Cannabinoids and Their Medicinal Properties. *Cannabis* Career Institute (Oct. 30, 2014), available at https://cannabiscareerinstitute.com/10-cannabinoids-and-their-medicinal-properties/; each of which is incorporated herein by reference in their entireties.

A nasal multi-dose dispenser device according to embodiments of the present invention, such as the Albion or Digital airless applicator systems available from Airlessystems, is comprised of a fluid container and a distributor pump for delivery of multiple doses of a gel or other topical formulation. In one embodiment of the present invention, the nasal multi-dose dispenser device is adapted for an airless fluid dispensing system. In another embodiment of the present invention, the nasal multi-dose dispenser device is adapted for a dip tube fluid dispensing system.

An example of an airless system that is contemplated by the present invention is one that will deliver a liquid, including gel, without the need for a pressured gas or air pump to be in contact with the liquid (or gel). In general, an airless system of the present invention comprises a flexible pouch containing the liquid, a solid cylindrical container a moving piston, an aspirating pump, a dosing valve and a delivery nozzle, as depicted, for example, in FIGS. 1-4.

In accordance with the present invention, the multi-dose dispenser 100 of FIG. 1 is provided with a fluid container 120, a distributor pump 140 and a cap 102. Fluid container 120 comprises a container body 122, a base 124 and a neck 126. The distributor pump 140 is fastened to the neck by a sleeve 128. The top end of the container body 122 is closed by the distributor pump 140. The sleeve 128 tightly pinches a neck gasket 150 against the top end of the container body 122. The container body 122 forms a vacuum and houses the fluid to be dispensed.

The distributor pump 140 is closed by its actuator nozzle 130, which retains the stem 144 at the stem head. The actuator nozzle 130 comprises an outlet channel 132 and tip 134.

The actuator nozzle 130 is shaped to conform with the interior surface of a user's nostril. The actuator nozzle 130 is moveable between a downward open position and upward closed position. The user removes the cap 102 and inserts the actuator nozzle 130 in the user's nostril. When the user pushes the actuator nozzle 130 downwards to the open position, fluid in the dosing chamber 180 is withdrawn by the distributor pump 140 and exits at the tip 134 via the outlet channel 132 of the actuator nozzle 130.

Figure 2:
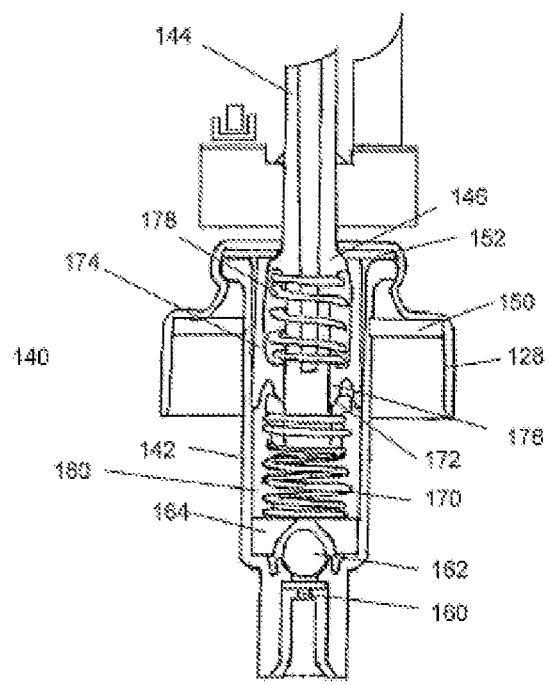
FIG. 2 is a cross-sectional side view of the distributor pump of the first embodiment of the invention.

FIG. 2 shows a cross-sectional view of the distributor pump 140. The distributor pump has a body 142 provided with a bottom intake having an inlet valve 160 with a ball 162 as its valve member. The ball 162 is held in place by a cage 164 and by a return spring 170.

At its bottom end, the stem 144 carries a spring cap 172. A piston 174 is located above the spring cap 172. The stem 144 passes through an axial orifice of the piston base 176. The side walls of the piston 174 seals against the distributor pump body 142 via lips. The sleeve 128 tightly pinches a stem gasket 152 against the stem collar 146, distributor pump body 142 and top of the piston 174. A precompression spring 178 placed between the piston base 176 and the stem collar 146. The precompression spring 178 biases the actuator nozzle 130 via the stem 144 to the closed position. The return spring 170, which returns the piston 174 back upwards, is compressed between two opposed seats on the cage 164 and the spring cap 172.

The distributor pump 140 has a dosing chamber 180 formed between the cage 164 and piston 174. When the user pushes the actuator nozzle downwards to the open position, fluid in the dosing chamber is withdrawn by the distributor pump 140 and dispensed from the tip of the actuator nozzle 130.

When the user releases the actuator nozzle 130 upwards to the closed position, a fluid in the container body 122 is withdrawn into the dosing chamber 180 by the distributor pump 140. Thus, a dose of fluid is ready for the next actuation of the actuator nozzle by the user.

Figure 3:
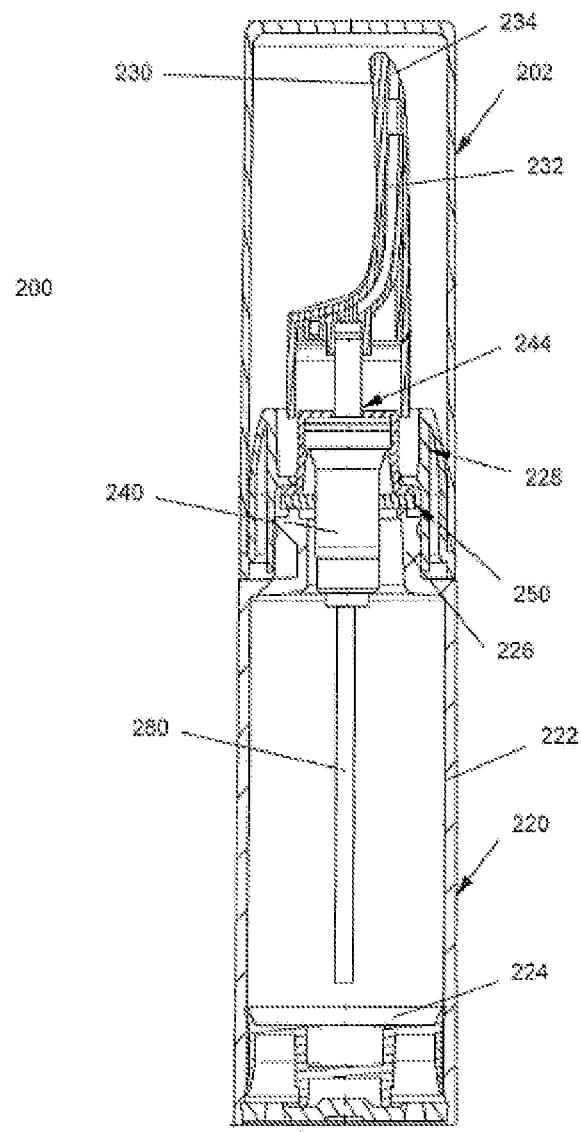
FIG. 3 is a side view of a second embodiment of a distributor pump of the invention.

In another embodiment of the present invention, the dispenser 200 of FIG. 3 is provided with a fluid container 220, a distributor pump 240 and a cap 202. The fluid container 220 comprises a container body 222, a base 224 and a neck 226. The distributor pump 240 is fastened to the neck by a sleeve 228. The top end of the container body 222 is closed by the distributor pump 240. The sleeve 228 tightly pinches a neck gasket 250 against the top end of the container body 222. The container body 222 houses the fluid to be dispensed.

The distributor pump 240 is closed by its actuator nozzle 230, which retains the stem 244 at the stem head. The actuator nozzle 230 comprises an outlet channel 232 and tip 234. The actuator nozzle 230 is shaped to conform with the interior surface of a user's nostril. The actuator nozzle 230 is moveable between a downward open position and upward closed position. The user removes the cap 202 and inserts the actuator nozzle 230 in the user's nostril. When the user pushes the actuator nozzle 230 downwards to the open position, fluid in the dosing chamber 280 is withdrawn by the distributor pump 240 and exits at the tip 234 via the outlet channel 232 of the actuator nozzle 230.

Figure 4:
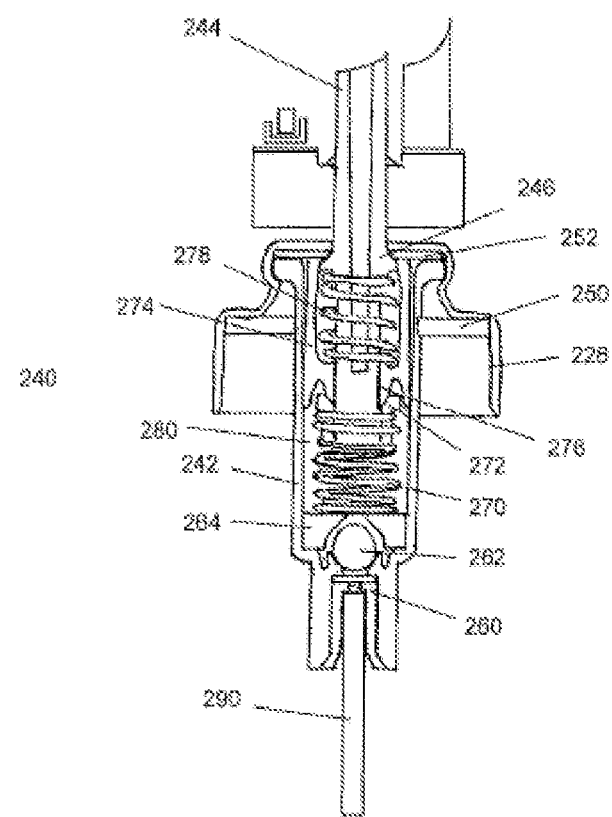
FIG. 4 is a cross-sectional side view of the distributor pump of the second embodiment of the invention.
Figure 5:
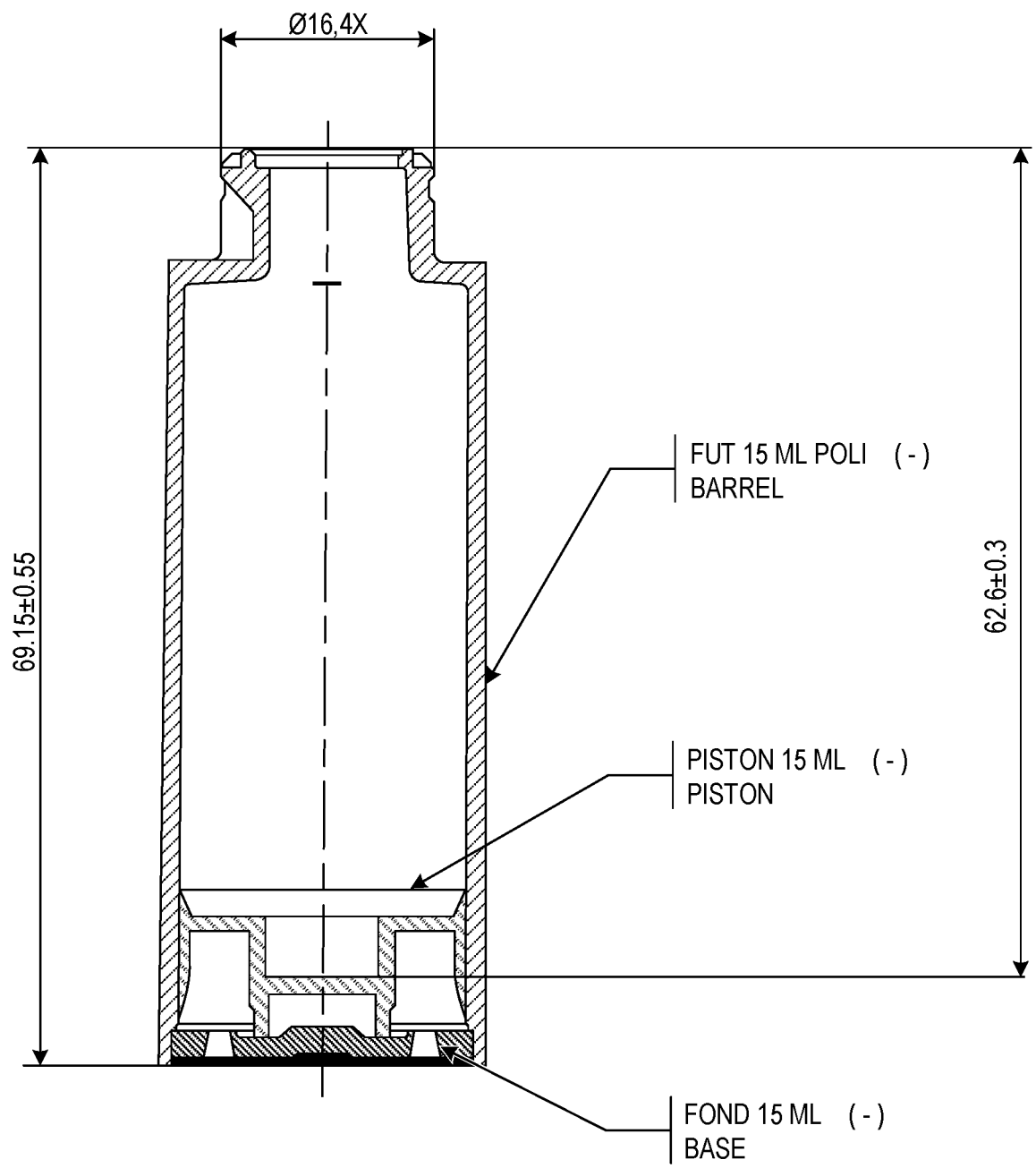
FIG. 5 is a side view of a second embodiment of a distributor pump of the invention concerning an airless bottle assembly of the invention.
Figure 6:
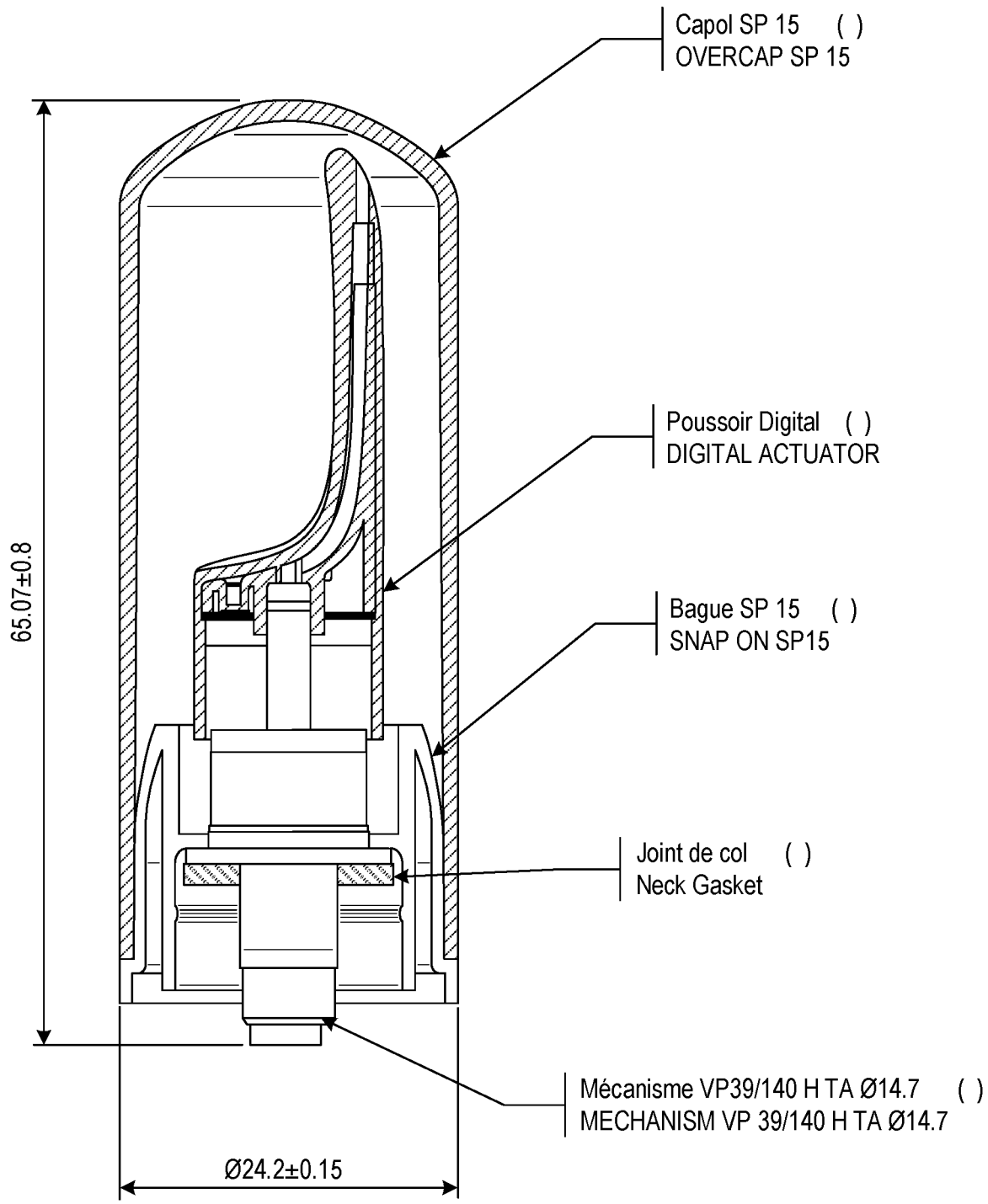
FIG. 6 is a side view of a second embodiment of a distributor pump of the invention concerning digital actuator and rounded cap.
Figure 7B:
Figure 7B:
Figure 7B:

FIG. 4 shows a cross-sectional view of the distributor pump 240. The distributor pump has a body 242 provided with a bottom intake having an inlet valve 260 with a ball 262 as its valve member. The ball 262 is held in place by a cage 264 and by a return spring 270. Optionally, a dip tube 290 can extend downward from the inlet valve 260 and is immersed in the liquid contained in the container body.

At its bottom end, the stem 244 carries a spring cap 272. A piston 274 is located above the spring cap 272. The stem 244 passes through an axial orifice of the piston base 276.

The side walls of the piston 274 seals against the distributor pump body 242 via lips. The sleeve 228 tightly pinches a stem gasket 252 against the stem collar 246, distributor pump body 242 and top of the piston 274.

A precompression spring 278 placed between the piston base 276 and the stem collar 246. The precompression spring 278 biases the actuator nozzle 230 via the stem 244 to the closed position.

The return spring 270, which returns the piston 274 back upwards, is compressed between two opposed seats on the cage 264 and the spring cap 272.

The distributor pump 240 has a dosing chamber 280 formed between the cage 264 and piston 274. When the user pushes the actuator nozzle downwards to the open position, air enters the dosing chamber 280, which forces the fluid in the dosing chamber to be withdrawn by the distributor pump 240 and dispensed from the tip of the actuator nozzle 230.

When the user releases the actuator nozzle 230 upwards to the closed position, the air contained in the dosing chamber 280 forces the fluid in the container body 222 to be withdrawn into the dosing chamber 280. Thus, a dose of fluid is ready for the next actuation of the actuator nozzle by the user.

The amount of fluid withdrawn by the distributor pump into the dosing chamber may be a fixed volume. The distributor pumps may be of a variety of sizes to accommodate a range of delivery volumes. For example, a distributor pump may have a delivery volume of up to about 150 μl. See FIGS. 1-6.

The dispensers of the present invention may dispense topical intranasal cannabinoid pharmaceutical compositions, preferably pernasally, such as in the form of a cream, gel or viscous emulsion and, in particular a thixotropic cream, gel and viscous emulsion.

Examples of various embodiments of the present invention will now be further illustrated with reference to the following examples. Thus, the following examples are provided to illustrate the invention, but are not intended to be limiting thereof. Parts and percentages are by weight unless otherwise specified.

EXAMPLES

Example 1: 15.5% Cannabinoids in a Castor Oil Based Composition

Heat Castor Oil to about 50° C. Dissolve THC and CBD in this heated Castor Oil under inert atmosphere. Add Colloidal Silicon Dioxide and homogenize to break any lumps. Apply vacuum with continuous mixing to remove any entrapped air. Add Oleoyl Polyoxylglycerides and continue mixing under vacuum. Release the vacuum with Nitrogen and cool the product to below about 30° C. with slow mixing. Ingredients are mixed in the proportions listed in Table 1, below.

| Ingredients | Function | % w/w |
|---|---|---|
| Tetrahydrocannabinol | Active | 0.02 |
| Cannabidiol | Active | 15.48 |
| Castor Oil | Oily Vehicle | 76.50 |
| Colloidal Silicon Dioxide | Thickening agent | 4.00 |
| Oleoyl Polyoxylglycerides | Surfactant/Wetting Agent | 4.00 |
| Total | | 100 |

Example 2: 15.5% Cannabinoids in Castor Oil-Based Composition

Heat Castor Oil to about 50° C. Dissolve THC and CBD in this heated Castor Oil under inert atmosphere. Apply vacuum with continuous mixing to remove any entrapped air. Add Oleoyl Polyoxylglycerides and continue mixing under vacuum. Release the vacuum with Nitrogen and cool the product to below about 30° C. with slow mixing. Ingredients are mixed in the proportions listed in Table 2, below.

| Ingredients | Function | % w/w |
|---|---|---|
| Tetrahydrocannabinol | Active | 15.48 |
| Cannabidiol | Active | 0.02 |
| Castor Oil | Oily Vehicle | 80.50 |
| Oleoyl Polyoxylglycerides | Surfactant/Wetting Agent | 4.00 |
| Total | | 100.00 |

Example 3: Sucrose Acetate Isobutyrate Based Composition with 15.5% Cannabinoids Heat Sucrose Acetate Isobutyrate to about 50° C. Add and mix Medium Chain Triglycerides, Polyoxyl 35 Hydrogenated Castor Oil and Oleoyl Polyoxylglycerides under inert atmosphere. Add and dissolve THC and CBD to make a clear solution. Ingredients are mixed in the proportions listed in Table 3, below.

| Ingredients | Function | % w/w |
|---|---|---|
| Tetrahydrocannabinol | Active | 0.02 |
| Cannabidiol | Active | 15.48 |
| Sucrose Acetate Isobutyrate | Oily Vehicle | 50.00 |
| Medium Chain Triglycerides | Emollient | 30.50 |
| Polyoxyl 35 Hydrogenated Castor Oil | Surfactant/Wetting Agent | 2.00 |
| Oleoyl Polyoxylglycerides | Surfactant/Wetting Agent | 2.00 |
| Total | | 100.00 |

Example 4: 16% Cannabinoid in Castor Oil

Heat Sucrose Acetate Isobutyrate to about 50° C. Add and mix medium chain triglycerides, Polyoxyl 35 Hydrogenated Castor Oil and Oleoyl Polyoxylglycerides under inert atmosphere. Add and dissolve THC and CBD to make a clear solution. Ingredients are mixed in the proportions listed in Table 4, below.

| Ingredients | Function | % w/w |
|---|---|---|
| Tetrahydrocannabinol | Active | 8.00 |
| Cannabidiol | Active | 8.00 |
| Sucrose Acetate Isobutyrate | Oily Vehicle | 50.00 |
| Medium Chain Triglycerides | Oily Vehicle | 30.00 |
| Polyoxyl 35 Hydrogenated Castor Oil | Surfactant/Wetting Agent | 2.00 |
| Oleoyl Polyoxylglycerides | Surfactant/Wetting Agent | 2.00 |
| Total | | 100.00 |

Example 5: Oil in Water Based Emulsion Containing about 2% Cannabinoids

Heat Seasame Oil and Castor Oil to about 55-60° C. Add Polyoxyl 35 Hydrogenated Castor Oil and Oleoyl Polyoxylglycerides, Methylparaben and Propylparaben and continue mixing to make a clear solution. Add and dissolve THC and CBD with continuous mixing and homogenization.

Add Dextrose in water that is heated to about 55° C. and mix to dissolve. Then disperse Carbopol using a homogenizer. Add oily phase to this aqueous phase and continue mixing and homogenizing to form a uniform emulsion. Adjust the pH of the gel to about 7.4 using about 1N NaOH with continuous mixing. Cool the product to below about 30° C. while mixing. Ingredients are mixed in the proportions listed in Table 5, below.

| Ingredients | Function | % w/w |
|---|---|---|
| Tetrahydrocannabinol | Active | 1.00 |
| Cannabidiol | Active | 1.00 |
| Sesame Oil | Oily Vehicle | 10.00 |
| Castor Oil | Oily Vehicle | 4.00 |
| Oleoyl Polyoxylglycerides | Surfactant/Wetting Agent | 4.00 |
| Polyoxyl 35 Hydrogenated Castor Oil | Emulsifier | 2.00 |
| Methylparaben | Preservative | 0.10 |
| Propylparaben | Preservative | 0.05 |
| Dextrose | Tonicity adjuster | 3.60 |
| Carbomer 934P | Thickening agent | 0.35 |
| Sodium Hydroxide | pH adjustment | 0.00 |
| Purified Water | Solvent | 73.90 |
| Total | | 100.00 |

Example 6: 2.5% Cannabinoid in Emulsion

Heat Sesame Oil and Olive Oil to about 55-60° C. Add Polyoxyl 35 Hydrogenated Castor Oil, Oleoyl Polyoxyglycerides, Methylparaben and Propylparaben and continue mixing to make a clear solution. Add and dissolve THC and CBD with continuous mixing and homogenization.

Add Hydroxypropylcellulose in water that is heated to about 55° C. and mix to form uniform suspension. Then add Dextrose and mix to dissolve using a homogenizer. Add oily phase to this aqueous phase and continue mixing and homogenizing to form a uniform emulsion.

All processing should be performed under inert atmosphere. Ingredients are mixed in the proportions listed in Table 6, below.

| Ingredients | Function | % w/w |
|---|---|---|
| Tetrahydrocannabinol | Active | 2.44 |
| Cannabidiol | Active | 0.06 |
| Sesame Oil | Oily Vehicle | 10.00 |
| Olive Oil | Oily Vehicle | 4.00 |
| Oleoyl Polyoxylglycerides | Surfactant/Wetting Agent | 4.00 |
| Polyoxyl 35 Hydrogenated Castor Oil | Emulsifier | 2.00 |
| Methylparaben | Preservative | 0.10 |
| Propylparaben | Preservative | 0.05 |
| Dextrose | Tonicity adjuster | 3.60 |
| Hydroxypropylcellulose | Thickener | 3.00 |
| Purified Water | Solvent | 70.75 |
| Total | | 100.00 |

Example 7: 5% Cannabinoids in SAIB Based Gel

Heat Sucrose Acetate Isobutyrate to about 50° C. under inert atmosphere. Add and mix Coconut oil, Glycerylmonostearate and Oleoyl Polyoxylglycerides. Add and dissolve THC and CBD to make a clear solution. Ingredients are mixed in the proportions listed in Table 7, below.

| Ingredients | Function | % w/w |
|---|---|---|
| Tetrahydrocannabinol | Active | 3.75 |
| Cannabidiol | Active | 1.25 |
| Sucrose Acetate Isobutyrate | Oily Vehicle | 50.00 |
| Coconut Oil | Emollient | 41.00 |
| Glcerylmonostearate | Surfactant/Wetting Agent | 2.00 |
| Oleoyl Polyoxylglycerides | Surfactant/Wetting Agent | 2.00 |
| Total | | 100.00 |

Example 8: 10% Cannabinoid in Castor Oil Gel

Castor Oil and Oleoyl Polyoxylglycerides are heated and then mixed. Silicon Dioxide is then added and further mixing is performed. Apply vacuum to remove any entrapped air in the gel. CBD is added and is dissolved upon mixing and with gently heating (to about 40° C.) under inert atmosphere. The gel is loaded into bottles for storage and syringes for administration. Ingredients are mixed in the proportions listed in Table 8, below.

| Ingredients | Function | % w/w |
|---|---|---|
| Tetrahydrocannabinol | Active | 2.00 |
| Cannabidiol | Active | 8.00 |
| Castor Oil | Oily Vehicle | 82.00 |
| Colloidal Silicon Dioxide | Thickening agent | 4.00 |
| Oleoyl Polyoxylglycerides | Surfactant/Wetting Agent | 4.00 |
| Total | | 100.00 |

Example 9: 20% Cannabinoid in Castor Oil-Gel

Combine about 120 g gel composition that is composed of 88 parts castor oil, 4 parts colloidal silica and 4 parts Labrafil®, with 14 g CBD and heat to about 50° C. with mixing until transparent and CBD is dissolved (visual inspection) (in Table 9 below). Remove from heat and using a cold water bath, cool the mixture while stirring. Put gel into syringes for use in PK study. Remaining gel is put into a bottle for storage and analysis.

| Ingredients | Function | % w/w |
|---|---|---|
| Cannabidiol | Active | 14 g |
| Caster Oil based gel composition | Solvent | 120 g |
| Total | | 134.00 |

Example 9B: 20% CBD in Castor Oil Gel Composition

Combined about 95 g gel composition that is composed of 88 parts castor oil, 4 parts colloidal silica and 4 parts Labrafil®, with 23.8 g CBD and heat to about 40° C. with mixing until transparent and CBD is dissolved (visual inspection) (in Table 9). Removed from heat and using a cold water bath, cool the mixture while stirring. Fill syringes with gel for use in PK study. Store remaining gel in a bottle for analysis.

Example 9C: 16% CBD in Castor Oil Gel Composition

Combined about 90 g gel composition from example 9B and 22.5 g (inactive) gel composition that is composed of 88 parts castor oil, 4 parts colloidal silica and 4 parts Labrafil BD and heat to about 40° C. with mixing until transparent and CBD is dissolved (visual inspection) (in Table 9). Remove from heat and using a cold water bath, cool the mixture while stirring. Fill syringes with gel for use in PK study. Store remaining gel in a bottle for analysis.

Though castor oil is traditionally thought of as an oily vehicle, it is found that castor oil has sufficient wetting agent properties to be a dual-use compound. Heat Castor Oil to about 50° C. under inert atmosphere. Add THC and CBD and dissolve to make a clear oily solution. Ingredients are mixed in the proportions listed in Table 10, below.

| Ingredients | Function | % w/w |
|---|---|---|
| Tetrahydrocannabinol | Active | 0.10 |
| Cannabidiol | Active | 19.90 |
| Castor Oil | Oily vehicle AND wetting agent | 80.00 |
| Total | | 100.00 |

Example 10: 0.4% Cannabinoids in Castor Oil

Heat Castor Oil to about 50° C. under inert atmosphere. Add THC and CBD and dissolve to make a clear oily solution. Ingredients are mixed in the proportions listed in Table 11, below.

| Ingredients | Function | % w/w |
|---|---|---|
| Tetrahydrocannabinol | Active | 0.20 |
| Cannabidiol | Active | 0.20 |
| Castor Oil | Oily vehicle AND wetting agent | 99.60 |
| Total | | 100.00 |

Example 11: 4% Cannabinoids in Water in Oil (W/O) Emulsion

Heat Coconut oil to about 55-60° C. under inert atmosphere. Add Glycerylmonostearate, Beeswax, Oleoyl Polyoxylglycerides, Methylparaben and Propylparaben and continue mixing to make a clear solution. Add and dissolve THC and CBD with continuous mixing and homogenization.

Add Purified Water, heat to about 55° C., to this oily phase and continued mixing and homogenizing to form a uniform emulsion. Cool to below about 30° C. while mixing. Ingredients are mixed in the proportions listed in Table 12, below.

| Ingredients | Function | % w/w |
|---|---|---|
| Tetrahydrocannabinol | Active | 2.00 |
| Cannabidiol | Active | 2.00 |
| Beeswax | Thickening agent | 5.00 |
| Coconut Oil | Oily vehicle | 50.00 |
| Glycerylmonostearate | Surfactant/Wetting Agent | 3.00 |
| Oleoyl Polyoxylglycerides | Surfactant/Wetting Agent | 2.00 |
| Methylparaben | Preservative | 0.10 |
| Propylparaben | Preservative | 0.05 |
| Purified Water | Solvent | 35.85 |
| Total | | 100.00 |

Example 12: 10% CBD in a Castor-Oil Based Composition

Castor oil and oleoyl polyoxylglycerides are mixed together thoroughly. CBD is added and is dissolved upon mixing to form a clear gel or a viscous solution. The gel is deaerated under vacuum and is loaded into tubes for storage and administration. Ingredients are mixed in the proportions listed in Table 13, below.

| Ingredient | Function | % w/w |
|---|---|---|
| CBD | Active ingredient | 10 |
| Castor Oil | Oily Vehicle | 86 |
| Oleoyl Polyoxylglycerides | Surfactant/Wetting Agent | 4 |
| Total | | 100 |

Example 13: 10% CBD in Sesame Oil-Based Composition

Sesame oil and oleoyl polyoxylglycerides are mixed together thoroughly. Silicon dioxide is then added and further mixing is performed. CBD is then added and is dissolved upon mixing with gentle heating (to about 40° C.). The resultant gel is deaerated under vacuum and is loaded into tubes for storage or syringes for administration. Ingredients are mixed in the proportions listed in Table 14, below.

| Ingredient | Function | % w/w |
|---|---|---|
| CBD | Active ingredient | 10 |
| Sesame Oil | Oily Vehicle | 86 |
| Oleoyl Polyoxylglycerides | Surfactant/Wetting Agent | 2 |
| Silicon Dioxide | Thickener | 2 |
| Total | | 100 |

Example 14: Emulsified Composition of 12% CBD in Mixture of Oils

Sesame oil, olive oil, oleoyl polyoxylglycerides and polyoxyl 40 hydrogenated castor oil are mixed together thoroughly. CBD is added and is dissolved with mixing (Oil Phase). In a separate vessel, hydroxypropyl cellulose is added to water, and is mixed to form a viscous liquid (Aqueous Phase). The Aqueous Phase is added to the Oil Phase and homogenized to create a cream, which is then deaerated using vacuum and is then loaded into tubes for storage and administration. Ingredients are mixed in the proportions listed in Table 15, below.

| Ingredient | Function | % w/w |
|---|---|---|
| CBD | Active ingredient | 12 |
| Sesame Oil | Oily Vehicle | 20 |
| Olive Oil | Oily Vehicle | 20 |
| Oleoyl Polyoxylglycerides | Wetting Agent | 2 |
| Polyoxyl 40 Hydrogenated Castor Oil | Surfactant | 2 |
| Hydroxypropyl Cellulose | Thickener | 4 |
| Water | Solvent | 40 |
| Total | | 100 |

Example 15: 20% CBD in Sesame Oil

Castor Oil and Oleoyl polyoxylglycerides are mixed and silicone dioxide is then added and further mixing is performed. CBD is added and is dissolved upon mixing and with gently heating (to about 40° C.). The resultant gel is deaerated under vacuum and is then loaded into tubes for storage or syringes for administration. Ingredients are mixed in the proportions listed in Table 16, below.

| Ingredient | Function | % w/w |
|---|---|---|
| CBD | Active ingredient | 20 |
| Sesame Oil | Oily Vehicle | 73.4 |
| Oleoyl Polyoxylglycerides | Wetting Agent | 3.3 |
| Silicon Dioxide | Thickener | 3.3 |
| Total | | 100 |

Example 16: 10% CBD in SAIB Mixture

Though SAIB is traditionally thought of as a vehicle, it also has sufficient wetting agent properties to be a dual-use compound. SAIB is heated to about 40° C. and is then poured into a beaker. CBD is added and is dissolved upon mixing with gently heating (at about 40° C.). The gel is loaded into vials for storage. The resulting product is a very viscous liquid. Ingredients are mixed in the proportions listed in Table 17, below.

| Ingredient | Function | % w/w |
|---|---|---|
| CBD | Active ingredient | 10 |
| SAIB | Oily vehicle AND wetting agent | 90 |
| Total | | 100 |

Example 17: 10% CBD in SAIB Mixture

SAIB is heated to about 40° C. and then poured into a beaker. The medium chain triglycerides and Cremophore EL are added and are mixed until homogeneous. This is followed by the addition of CBD which is dissolved upon mixing with gently heating (at about 40° C.). The resultant gel/viscous solution is deaerated under vacuum and is then loaded into vials for storage or syringes for administration. Ingredients are mixed in the proportions listed in Table 18, below.

| Ingredient | Function | % w/w |
|---|---|---|
| CBD | Active ingredient | 10 |
| SAIB | Oily Vehicle | 50 |
| Medium Chain Triglycerides | Oily Vehicle | 35 |
| Cremophore EL | Wetting agent | 5 |
| Total | | 100 |

Example 18: 20% CBD in SAIB

SAIB is heated to about 40° C. and is then poured into a beaker. The medium chain triglycerides and Cremophore EL are added and are mixed until homogeneous. This is followed by the addition of CBD which is dissolved upon mixing with gently heating (at about 40° C.). The resultant gel/viscous solution is deaerated under vacuum and is then loaded into vials for storage or syringes for administration. Ingredients are mixed in the proportions listed in Table 19, below.

| Ingredient | Function | % w/w |
|---|---|---|
| CBD | Active ingredient | 20 |
| SAIB | Oily Vehicle | 44.5 |
| Medium Chain Triglycerides | Fluidifying agent/Oily vehicle | 31 |
| Oleoyl Polyoxylglycerides | Wetting agent | 4.5 |
| Total | | 100 |

Example 19: 10% CBD in Castor Oil

Castor oil and oleoyl polyoxylglycerides are mixed and then silicone dioxide is added and further mixing is performed. CBD is added and is dissolved upon mixing and with gently heating (to about 40° C.). The gel is loaded into bottles for storage and syringes for administration. Ingredients are mixed in the proportions listed in Table 20, below.

| Ingredient | Function | % w/w |
|---|---|---|
| CBD | Active ingredient | 10 |
| Castor Oil | Oily Vehicle | 86 |
| Oleoyl Polyoxylglycerides | Surfactant/Wetting Agent | 2 |
| Silicon Dioxide | Thickener | 2 |
| Total | | 100 |

Example 20: 20% CBD in Castor Oil-Gel

Castor oil and Oleoyl polyoxylglycerides are mixed and then silicone dioxide is added and further mixing is performed. CBD is added and is dissolved upon mixing and with gently heating (to about 40° C.). The resultant gel is loaded into bottles for storage and syringes for administration. Ingredients are mixed in the proportions listed in Table 21, below.

| Ingredient | Function | % w/w |
|---|---|---|
| CBD | Active ingredient | 20 |
| Castor Oil | Oily Vehicle | 73.4 |
| Oleoyl Polyoxyglycerides | Surfactant/Wetting Agent | 3.3 |
| Silicon Dioxide | Thickener | 3.3 |
| Total | | 100 |

Example 21: Pharmaceutical Product with Cannabinoids

About 5 grams of a Composition according to the previous 18 examples are each loaded into a collapsible tube shaped multidose dispenser equipped with a metered-dose pump dispensing about 70 µL per actuation. The dispenser contains an elongated nozzle end which allows the composition to be applied in the nasal vestibule of a nostril. The pump is manually primed by actuating the pump. The pump is used to nasally administer a cannabinoid or a cannabinoid mixture to a patient in need thereof.

Example 22: Pharmacokinetics of Cannabinoid Administration

Figure 8:
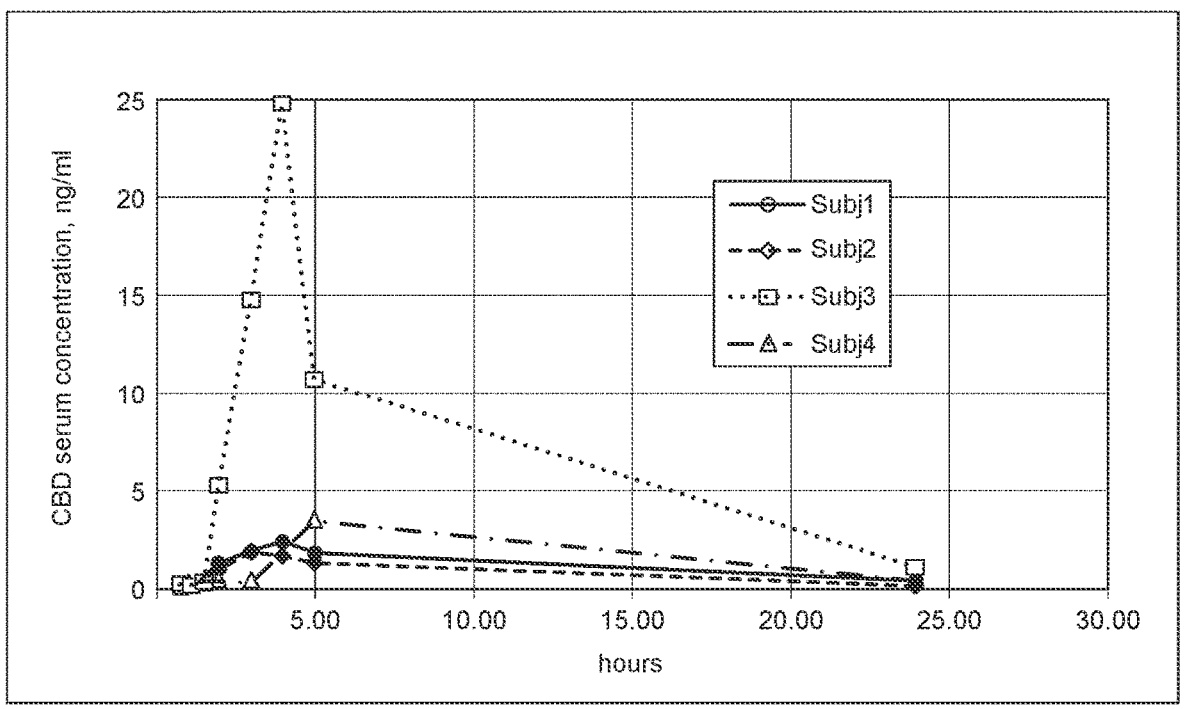
FIG. 8 depicts a pharmacokinetic analysis of Composition Examples 9A (20% CBD gel, N=2, Subj #1 and #2) and 9B (10% CBD gel, N=2 Subj #3 and #4) after administration to healthy volunteer subjects. (See Example 22).

Pharmacokinetics of CBD gel from Example 9A and 9B is performed in 4 healthy volunteers. Two subjects receive an approximate 25 mg dose of CBD contained in ca. 125 mg of the gel composition in Example 9B (20% CBD in Castor Oil; Subj #1 and #2) into a single nostril via syringe. Two other subjects received an approximate 25 mg dose of CBD contained in ca. 250 mg of the Composition in Example 9A (10% CBD in sesame oil; Subj #3 and #4), 125 mg per nostril, via syringe. Blood samples are taken at: pre-dose, about 15 min, 30 min, 45 min, 1 h, 2 h, 3 h, 4 h, 5 h and 24 h directly into tubes containing EDTA. Blood samples are centrifuged and serum is analyzed by LCMS for CBD. The following PK parameters are determined using a noncompartmental PK mode (Table 22, below, and FIG. 8).

| Subj # | Composition (example) applied | Weight of dose administered | Fasted? | Cmax, ng/ml | Tmax, h | AUC ng/ml h |
|---|---|---|---|---|---|---|
| 1 | 9B | 132 mg | Y | 2.45 | 4 | 47.3 |
| 2 | 9B | 126 mg | Y | 1.98 | 3 | 34.0 |
| 3 | 9A | 260 mg | N | 24.8 | 4 | 371.2 |
| 4 | 9A | 273 mg | Y | 3.58 | 5 | 55.8 |

Example 23: *Cannabis* Oil Composition for Nasal Application

About 250 g of dried *cannabis* is extracted with 2 L ethanol. After filtration, the ethanol is evaporated to leave a resinous material containing cannabinoids (10-60 g; >70% cannabinoids). About 90 g Grape seed oil is added to the resin. Vacuum, stirring and heat is applied until a homogenous mixture is obtained. About 6 g colloidal silica is added and dispersed using a high shear mixer while under vacuum over a period of about 1 h. About 4 g Labrafil® is added and is mixed under vacuum until homogeneous. The vessel is allowed to come to atmospheric pressure with input of nitrogen gas. The resulting product is removed from the vessel and placed in 5 ml and 15 ml dispensers.

Example 24: *Cannabis* Oil Composition for Nasal Application

About 250 g of dried *cannabis* is extracted using liquid CO2. After filtration, the CO2 is allowed to evaporate to leave a resinous material containing cannabinoids (about 10-60 g; about >70% cannabinoids). About 90 g Sesame oil is added to the resin. Vacuum, stirring and heat is applied until a homogenous mixture is obtained. About 5 g Labrafil® is added and is mixed under vacuum until homogeneous. About 5 g colloidal silica is added and is dispersed using a high shear mixer while under vacuum over a period of about 1 h. The vessel is allowed to come to atmospheric pressure with input of nitrogen gas. The resulting product is analyzed for cannabinoid content and diluted with additional sesame oil to achieve a concentration of about 3%. It is then removed from the vessel and is placed in 5 ml and 15 ml dispensers for use.

Example 25: *Cannabis* Oil in an Emulsion

About 50 g of a concentrated *cannabis* oil (6% cannabinoids in grapeseed oil) is dispersed into a mixture of about 3 g ethoxylated-castor oil and about 47 g water and the resulting spray emulsion is filled into 5 ml and 15 ml dispensers for use.

Example 26: *Cannabis* Oil in a Cream

About 50 g of a concentrated *cannabis* oil (6% cannabinoids in grapeseed oil) is dispersed into a mixture of about 3 g ethoxylated-castor oil, about 47 g water and about 0.35 g Carbomer 934P. The resulting cream is filled into 5 ml and 15 ml dispensers for use.

Example 27: Rheology Assessment

A composition according to example 9A was analyzed using a Brookfield model HB cone-plate rheometer (spindle CP41) with varying shear. Shear was cycled from low (0/sec) at start to high (128/sec) shear and then back to low shear over a period of 200 sec at 25 C. The viscosity initially recorded at 2900 cPs at low shear decreased to 370 cPs at highest shear and returned to 5750 cPs at the end of the cycle. Using the same apparatus and program, but with spindle CP52, the viscosity of the same sample could only be measured at low shear and showed a viscosity>30,000 cPs. Using a Brookfield model RVO6 viscometer and #6 spindle, and turning for 5 min prior to capturing a measure, the viscosity is measured as 5000 cPs for the same composition. This highlights the difficulty in stating precise viscosity values when referencing a pseudoplastic material according to certain composition examples.

Example 28: Indications

Pain.
Types of Pain and doses of THC (it is believed that CBD can reduce the high associated with THC).
  i. Acute pain: There is not general agreement that THC works here. Positive results have been observed with 65 mg THC from smoked *cannabis*
  ii. Chronic pain (including neuropathic pain): Typically 2.5-50 mg smoked THC per dose, with repeat dosing per day up to 100 mg/day
  iii. Cancer pain: typically 5-20 mg oral dose, with repeat dosing per day.
  iv. Fibromyalgia: typically 5-15 mg oral dose, up to 15 mg per day
  v. Can be used in conjunction with codeine or opioids as adjuncts and as a means to reduce doses of opioid THC (pure synthetic) or THC-rich *cannabis* extract, may optionally contain CBD in ratios up to 50%

3% THC is a specific legal limit in current Canadian *cannabis* regulations. The CBD content is not regulated and can vary depending on the strain. THC in *cannabis* for pain is typically at least 50% to 99% of the mixture of cannabinoids in *cannabis* extract and be >97% to >99% if considering pure synthetic THC.
  i. Dose: 1 mg-20 mg THC cannabinoids contained in volume of 70-150 µL of a nasal cannabinoid pharmaceutical composition of the present invention (ca. 0.6% to 30% THC) which is applied in a nostril;
  ii. Dose: preferably 1-10 mg THC cannabinoids contained in volume of 70-150 µL of the composition (ca. 0.6% to 7% THC) which is applied in a nostril
  iii. preferably cannabinoids comprising 3% of the composition and supply a dose of 2.1 mg to 4.5 mg of THC cannabinoids contained in volume within the range of 70-150 µL, prefer a volume of 70-125 µL, pref 100-125 µL, specifically 70 µL, 100 uL or 125 µL
  iv. Dose volume (70-150 µL) is applied inside the nasal vestibule, preferably to the (soft) tissues opposite the nasal septum just below the boney bridge section of the nose
  v. Dose (1-20 mg, for example) can be applied per nostril, to one or both nostrils (total dose is 1-40 mg, for example)

Composition
  i. Composition comprised of THC cannabinoids in an oily vehicle or SAIB (sucrose acetate isobutyrate)
  ii. Composition comprised of THC cannabinoids in an oily vehicle to which is added a sufficient wetting agent to allow spreading in the nose on the nasal mucosa
  iii. Wetting agent may be a mixture of wetting agents/surfactants
  iv. List of wetting agents (surfactants) is provided in specification
  v. Concentration of wetting agent or mixture of wetting agents comprises 1-10% by weight of the composition, preferably 1-5%, more preferably 2-4%
  vi. Composition comprised of THC cannabinoids in an oily vehicle to which is added a wetting agent and a rheology agent Rheology modifying agent increases viscosity and provides reversible or partially, reversible pseudoplastic or thixotropic, behavior such that the viscosity is lower (<1000 cPs) when dispensed and upon standing in the nose increases (>5000 cPs). Quantity of rheology modifying agents is adjusted to achieve a viscosity range of 5000-50,000 cPs), preferably, based on a specific method of measurement. Viscosity values are method dependent because with thixotropic/pseudoplastic materials, the viscosity is a function of energy (shear forces) applied when measuring.
  i. List of rheology modifying agents (surfactants) is provided in claims already
  ii. Some rheology modifying agents are added to emulsion type compositions
  iii. Some other rheology modifying agents can be added to the oil-based compositions, quantities may not be the same, but are typically <10%, <5%, >0.5%

Dispensers
  i. Unit dose able to deliver 70-150 µL to the nasal vestibule as described
  ii. Airless device
  iii. Manually actuated, 5 ml multidose dispenser with a nasal applicator comprises at least 60 individual metered doses of 70 µL pump
  iv. Manually actuated, 15 ml multidose dispenser with a nasal applicator comprises at least 90 individual metered doses of 125 µL pump
  v. Manually actuated, multidose dispenser with a nasal applicator comprises a metered dose 125 µL pump and has a nominal volume of 15 ml or 30 ml
  vi. Manually actuated, multidose dispenser with a nasal applicator comprises a metered close 70 µL pump and has a nominal volume of 5 ml
  vii. 100 µL volume is also preferred on 5, 15 or 30 ml dispenser
  viii. Nasal applicator through which is dispensed the composition such that the tip can reach into the nasal vestibule just up to (but below) the boney bridge of the nose when held in one hand (with finger on the pump) and when actuated places a 70-150 µL volume of the composition at that position. The composition is spread through an action of pinching the nose across the bridge and lightly massaging (image available)
  ix. A 30 ml multidose dispenser that comprises at least 224 individual metered doses of 100 µL-150 µL Epilepsy or Seizures
CBD (pure synthetic) or CBD-rich *cannabis* extract, may optionally contain THC in low ratios (<20%, preferably <10%, <5%)

Dose for nasal delivery is about 50 mg to 250 mg CBD per day, taken as multiple doses of
  i. Dose: 15 mg-75 mg CBD cannabinoids contained in volume of 70-150 µL of the composition (ca. 10% to 50% CBD) which is applied in the nose
  ii. Dose: preferably 20-50 mg CBD cannabinoids contained in volume of 70-150 µL of the composition (ca. 13% to 50% CBD) which is applied in the nose.

Schizophrenia

CBD (pure synthetic), as it contains no THC. Can be herbal extract but preferred to avoid THC which has negative consequences (AEs) in schizophrenia Dose: about 50 mg to 250 mg CBD per day, taken as multiple doses of
  i. Dose: 15 mg-75 mg CBD cannabinoids contained in volume of 70-150 µL of the composition (ca. 10% to 50% CBD) which is applied in the nose
  ii. Dose: preferably 20-50 mg CBD cannabinoids contained in volume of 70-150 µL of the composition (ca. 13% to 50% CBD) which is applied in the nose.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, abstracts, articles, websites, and other references mentioned herein are incorporated by reference in their entirety.

In case of conflict, the present specification, including definitions, will control.

In addition, the materials, methods, and examples are illustrative only and not intended to be limiting. Various modifications and alterations to this invention will become apparent to those skilled in the art without departing from the scope and spirit of this invention. Illustrative embodiments and examples are provided as examples only and are not intended to limit the scope of the present invention. From the foregoing, it will be appreciated that specific embodiments of the invention have been described herein for purposes of illustration, but that various modifications may be made without deviating from the scope of the invention. Accordingly, the invention is not limited except as by the appended claims.

What is claimed is:

1. A method of treating schizophrenia in a subject, comprising nasally administering a nasal pharmaceutical composition into at least one nostril of the subject at least once per day in an amount effective to treat the subject's schizophrenia and/or alleviate or reduce the subject's symptoms thereof, wherein, the nasal pharmaceutical composition comprises:
   (a) about 40% w/w of cannabidiol (CBD)
   (b) about 50% w/w of a pharmaceutically acceptable oily vehicle comprising medium chain triglycerides;
   (c) about 4% w/w of silicon dioxide;
   (d) a solvent; and
   (e) a pharmaceutically acceptable excipient that promotes absorption of the CBD into nasal tissues,
   wherein the nasal pharmaceutical composition is a semi-solid or viscous liquid nasal pharmaceutical composition having a viscosity within a viscosity range of between 500 cps and 100,000 cps.

2. The method of claim 1, wherein nasal administration comprises nasally administering the nasal pharmaceutical composition into at least one nostril of the subject at least once per day, at least twice per day, at least three times per day, or at least four times per day.

3. The method of claim 1, wherein the nasal pharmaceutical composition is administered to the subject at a dose within the dose range of about 50 µl to about 150 µl per nostril.

4. The method of claim 1, wherein the nasal pharmaceutical composition is formulated in a cream, or a gel.

5. The method of claim 1, wherein the nasal pharmaceutical composition is administered to the subject in a single dose.

6. The method of claim 1, wherein the nasal pharmaceutical composition is a non-oral formulation.

* * * * *